US008592177B2

(12) United States Patent
Bathe et al.

(10) Patent No.: US 8,592,177 B2
(45) Date of Patent: Nov. 26, 2013

(54) PROCESS FOR THE FERMENTATIVE PREPARATION OF ORGANIC CHEMICAL COMPOUNDS USING CORYNEFORM BACTERIA IN WHICH THE SUGR GENE IS PRESENT IN ATTENUATED FORM

(75) Inventors: Brigitte Bathe, Salzkotten (DE); Georg Thierbach, Bielefeld (DE); Volker Wendisch, Jülich (DE); Verena Engels, Elsdorf (DE); Bernhard Eikmanns, Ulm (DE); Bastian Blombach, Stettenhofen (DE)

(73) Assignees: Evonik Degussa GmbH, Essen (DE); Forschungszentrum Jülich GmbH, Jülich (DE)

( * ) Notice: Subject to any disclaimer, the term of this patent is extended or adjusted under 35 U.S.C. 154(b) by 0 days.

(21) Appl. No.: 13/355,531

(22) Filed: Jan. 21, 2012

(65) Prior Publication Data

US 2012/0214211 A1 Aug. 23, 2012

Related U.S. Application Data

(62) Division of application No. 12/232,610, filed on Sep. 19, 2008, now Pat. No. 8,133,714.

(60) Provisional application No. 60/960,375, filed on Sep. 27, 2007, provisional application No. 60/996,706, filed on Nov. 30, 2007.

(51) Int. Cl.
*C12P 13/04* (2006.01)
*C12P 13/08* (2006.01)
*C12P 13/06* (2006.01)
*C12P 1/00* (2006.01)
*C12N 1/21* (2006.01)

(52) U.S. Cl.
USPC ........ 435/41; 435/252.32; 435/115; 435/116; 435/106

(58) Field of Classification Search
USPC .................... 435/252.32, 440, 106, 115, 116; 530/350; 536/23.1
See application file for complete search history.

(56) References Cited

U.S. PATENT DOCUMENTS

| | | | |
|---|---|---|---|
| 4,368,266 A | 1/1983 | Tosaka et al. | |
| 4,554,391 A | 11/1985 | Klun et al. | |
| 4,728,610 A | 3/1988 | Kanegae et al. | |
| 2003/0219881 A1 | 11/2003 | Brigitte et al. | |
| 2005/0153402 A1 | 7/2005 | Pompejus et al. | |
| 2005/0220933 A1 | 10/2005 | Hong et al. | |
| 2007/0082031 A1 | 4/2007 | Lotter et al. | |

FOREIGN PATENT DOCUMENTS

| | | |
|---|---|---|
| DE | 10 2006 016 158 A1 | 4/2007 |
| EP | 1 767 616 A2 | 3/2007 |

OTHER PUBLICATIONS

Cocaign, et al., "Batch Kinetics of *Corynebacterium glutamicum* During Growth on Various Carbon Substrates: Use of Substrate Mixtures to Localise Metabolic Bottlenecks," *Appl. Microbiol. Biotechnol.* 40:526-530 (1993).
Dominguez, et al., "Simultaneous Consumption of Glucose and Fructose from Sugar Mixtures During Batch Growth of *Corynebacterium glutamicum*," *Appl. Microbiol. Biotechnol.* 47:600-603 (1997).
Dominguez, et al., "Carbon-Flux Distribution in the Central Metabolic Pathways of *Corynebacterium glutamicum* During Growth on Fructose," *Eur. J. Biochem.* 254:96-102 (1998).
Engels, et al.," The DeoR-Type Regulator SugR Represses Expression of *ptsG* in *Corynebacterium glutamicum*," *J. Bacteriol.* 189(8):2955-2966 (Apr. 2007).
Kalinowski, et al., "The Complete *Corynebacterium glutamicum* ATCC 13032 Genome Sequence and Its Impact on the Production of L-Aspartate-Derived Amino Acids and Vitamins," *J Biotechnol.* 104:5-25 (2003).
Kozak, "Initiation of translation in prokaryotes and eukaryotes," *Gene* 234(8):187-208 (Jul. 1999).
Nishio, et al., "Comparative Complete Genome Sequence Analysis of the Amino Acid Replacements Responsible for the Thermostability of *Corynebacterium effciens*," *Genome Res.* 13:1572-1579 (2003).
Radmacher, et al., "Linking Central Metabolism with Increased Pathway Flux: L-Valine Accumulation by *Corynebacterium glutamicum*," Appl. and Environ. Microbiol. 68(5):2246-2250 (May 2002).
Seffernick, et al., "Melamine Deaminase and Atrazine Chlorohydrolase: 98 Percent Identical but Functionally Different," *J. Bacteriol.* 183(8):2405-2410 (Apr. 2001).
Van Der Rest, et al., "A Heat Shock Following Electroporation Induces Highly Efficient Transformation of *Corynebacterium glutamicum* with Xenogenic Plasmid DNA," *Appl. Microbiol. Biotechnol.* 52:541-545 (1999).
Wendisch, et al., "Quantitative Determination of Metabolic Fluxes during Coutilization of Two Carbon Sources: Comparative Analyses with *Corynebacterium glutamicum* during Growth on Acetate and/or Glucose," *J. Bacteriol.* 182(11):3088-3096 (Jun. 2000).
Witkowski, et al., "Conversion of β-Ketoacyl Synthase to a Malonyl Decarboxylase by Replacement of the Active-Site Cysteine with Glutamine," *Biochemistry* 38(36)11643-11650 (1999).
Yukawa, et al. "Comparative Analysis of the *Corynebacterium glutamicum* Group and Complete Genome Sequence of Strain R," *Microbiol.* 153(4):1042-1058 (2007).
Zhou, et al., Global analysis of gene transcription regulation in prokaryotes, *Cell. Mol. Life Sci.* 63(19-20):2260-2290 (2006).
English language abstract for DE 10 2006 061 158 A1.
English language abstract for EP 1 767 616 A2.

*Primary Examiner* — Delia Ramirez
(74) *Attorney, Agent, or Firm* — Law Office of: Michael A. Sanzo, LLC

(57) ABSTRACT

The invention relates to a recombinant coryneform bacterium which secretes an organic chemical compound and in which the sugR gene which codes for a polypeptide having the activity of an SugR regulator has been attenuated. The invention further relates to a processes for using this bacterium for the fermentative preparation of organic chemical compounds.

20 Claims, 1 Drawing Sheet

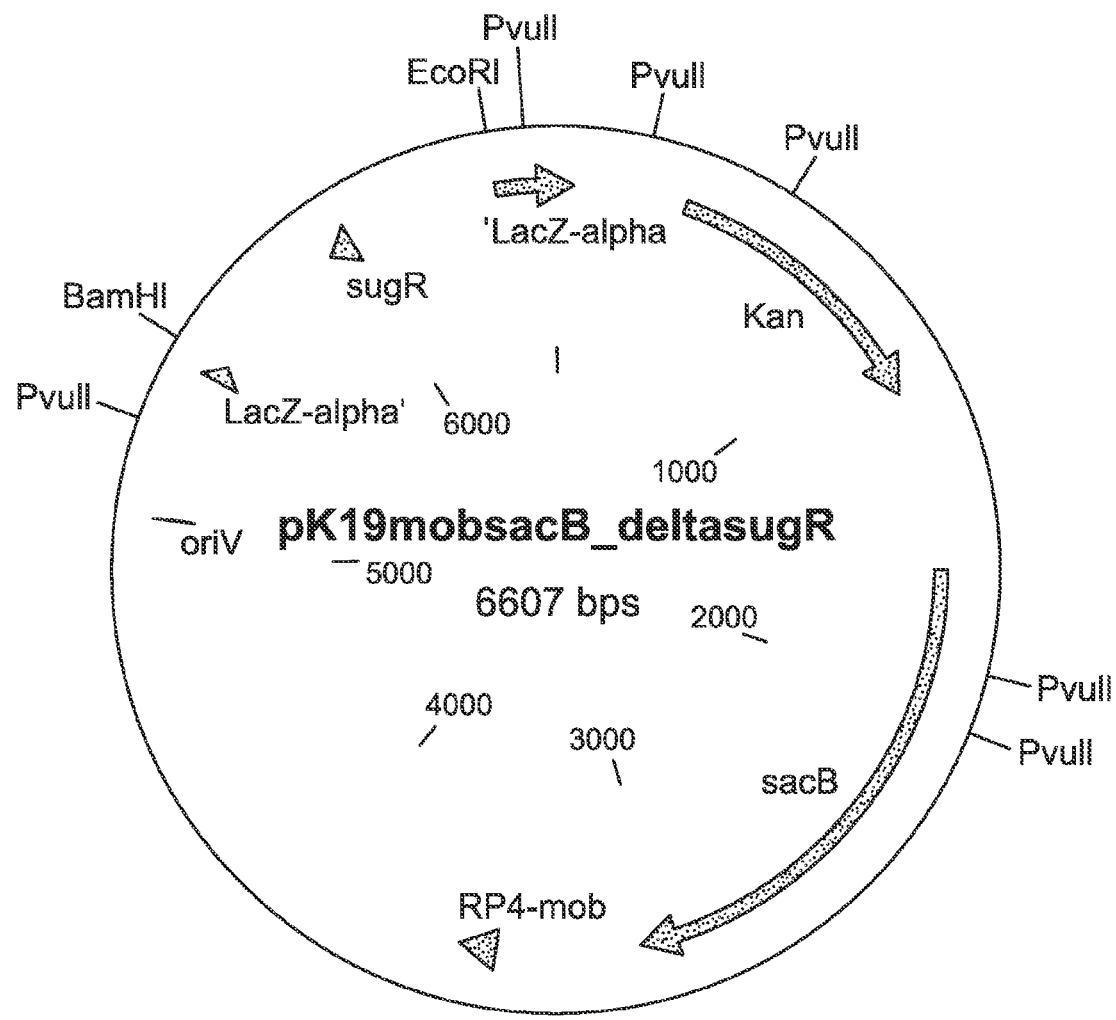

SEQUENCE LISTING

<160> NUMBER OF SEQ ID NOS: 20

<210> SEQ ID NO 1
<211> LENGTH: 780
<212> TYPE: DNA
<213> ORGANISM: Corynebacterium glutamicum
<220> FEATURE:
<221> NAME/KEY: CDS
<222> LOCATION: (1)..(777)

<400> SEQUENCE: 1

```
atg tac gca gag gag cgc cgt cga cag att gcc tca tta acg gca gtt        48
Met Tyr Ala Glu Glu Arg Arg Arg Gln Ile Ala Ser Leu Thr Ala Val
1               5                   10                  15 gag gga cgt gta aat gtc aca gaa tta gcg ggc cga ttc gat gtc act        96
Glu Gly Arg Val Asn Val Thr Glu Leu Ala Gly Arg Phe Asp Val Thr
                20                  25                  30 gca gag acg att cga cga gac ctt gcg gtg cta gac cgc gag gga att       144
Ala Glu Thr Ile Arg Arg Asp Leu Ala Val Leu Asp Arg Glu Gly Ile
            35                  40                  45 gtt cac cgc gtt cac ggt ggc gca gta gcc acc caa tct ttc caa acc       192
Val His Arg Val His Gly Gly Ala Val Ala Thr Gln Ser Phe Gln Thr
        50                  55                  60 aca gag ttg agc ttg gat act cgt ttc agg tct gca tcg tca gca aag       240
Thr Glu Leu Ser Leu Asp Thr Arg Phe Arg Ser Ala Ser Ser Ala Lys
65                  70                  75                  80 tac tcc att gcc aag gca gcg atg cag ttc ctg ccc gct gag cat ggc       288
Tyr Ser Ile Ala Lys Ala Ala Met Gln Phe Leu Pro Ala Glu His Gly
                85                  90                  95 gga ctg ttc ctc gat gcg gga act act gtt act gct ttg gcc gat ctc       336
Gly Leu Phe Leu Asp Ala Gly Thr Thr Val Thr Ala Leu Ala Asp Leu
            100                 105                 110 att tct gag cat cct agc tcc aag cag tgg tcg atc gtg acc aac tgc       384
Ile Ser Glu His Pro Ser Ser Lys Gln Trp Ser Ile Val Thr Asn Cys
        115                 120                 125 ctc ccc atc gca ctt aat ctg gcc aac gcc ggg ctt gat gat gtc cag       432
Leu Pro Ile Ala Leu Asn Leu Ala Asn Ala Gly Leu Asp Asp Val Gln
    130                 135                 140 ctg ctt gga gga agc gtt cgc gcg atc acc cag gct gtt gtg ggt gac       480
Leu Leu Gly Gly Ser Val Arg Ala Ile Thr Gln Ala Val Val Gly Asp
145                 150                 155                 160 act gcg ctt cgt act ctc gcg ctg atg cgt gcg gat gta gtg ttc atc       528
Thr Ala Leu Arg Thr Leu Ala Leu Met Arg Ala Asp Val Val Phe Ile
                165                 170                 175 ggc acc aac gcg ttg acg ttg gat cac gga ttg tct acg gcc gat tcc       576
Gly Thr Asn Ala Leu Thr Leu Asp His Gly Leu Ser Thr Ala Asp Ser
            180                 185                 190 caa gag gct gcc atg aaa tct gcg atg atc acc aac gcc cac aag gtg       624
Gln Glu Ala Ala Met Lys Ser Ala Met Ile Thr Asn Ala His Lys Val
        195                 200                 205 gtg gtg ttg tgt gac tcc acc aag atg ggc acc gac tac ctc gtg agc       672
Val Val Leu Cys Asp Ser Thr Lys Met Gly Thr Asp Tyr Leu Val Ser
    210                 215                 220 ttt ggc gca atc agc gat atc gat gtg gtg gtc acc gat gcg ggt gca       720
Phe Gly Ala Ile Ser Asp Ile Asp Val Val Val Thr Asp Ala Gly Ala
225                 230                 235                 240 cca gca agt ttc gtt gag cag ttg cga gaa cgc gat gta gaa gtt gtg       768
Pro Ala Ser Phe Val Glu Gln Leu Arg Glu Arg Asp Val Glu Val Val
                245                 250                 255 att gca gaa tga                                                        780
Ile Ala Glu
```

Ile Ala Glu

<210> SEQ ID NO 2
<211> LENGTH: 259
<212> TYPE: PRT
<213> ORGANISM: Corynebacterium glutamicum

<400> SEQUENCE: 2

```
Met Tyr Ala Glu Glu Arg Arg Gln Ile Ala Ser Leu Thr Ala Val
1               5                   10                  15

Glu Gly Arg Val Asn Val Thr Glu Leu Ala Gly Arg Phe Asp Val Thr
                20                  25                  30

Ala Glu Thr Ile Arg Arg Asp Leu Ala Val Leu Asp Arg Glu Gly Ile
                35                  40                  45

Val His Arg Val His Gly Gly Ala Val Ala Thr Gln Ser Phe Gln Thr
        50                  55                  60

Thr Glu Leu Ser Leu Asp Thr Arg Phe Arg Ser Ala Ser Ser Ala Lys
65                  70                  75                  80

Tyr Ser Ile Ala Lys Ala Ala Met Gln Phe Leu Pro Ala Glu His Gly
                85                  90                  95

Gly Leu Phe Leu Asp Ala Gly Thr Thr Val Thr Ala Leu Ala Asp Leu
                100                 105                 110

Ile Ser Glu His Pro Ser Ser Lys Gln Trp Ser Ile Val Thr Asn Cys
                115                 120                 125

Leu Pro Ile Ala Leu Asn Leu Ala Asn Ala Gly Leu Asp Asp Val Gln
                130                 135                 140

Leu Leu Gly Gly Ser Val Arg Ala Ile Thr Gln Ala Val Val Gly Asp
145                 150                 155                 160

Thr Ala Leu Arg Thr Leu Ala Leu Met Arg Ala Asp Val Val Phe Ile
                165                 170                 175

Gly Thr Asn Ala Leu Thr Leu Asp His Gly Leu Ser Thr Ala Asp Ser
                180                 185                 190

Gln Glu Ala Ala Met Lys Ser Ala Met Ile Thr Asn Ala His Lys Val
                195                 200                 205

Val Val Leu Cys Asp Ser Thr Lys Met Gly Thr Asp Tyr Leu Val Ser
                210                 215                 220

Phe Gly Ala Ile Ser Asp Ile Asp Val Val Thr Asp Ala Gly Ala
225                 230                 235                 240

Pro Ala Ser Phe Val Glu Gln Leu Arg Glu Arg Asp Val Glu Val Val
                245                 250                 255

Ile Ala Glu
```

<210> SEQ ID NO 3
<211> LENGTH: 2780
<212> TYPE: DNA
<213> ORGANISM: Corynebacterium glutamicum
<220> FEATURE:
<221> NAME/KEY: misc_feature
<222> LOCATION: (1)..(1000)
<223> OTHER INFORMATION: DNA sequence located upstream
<220> FEATURE:
<221> NAME/KEY: misc_feature
<222> LOCATION: (941)..(946)
<220> FEATURE:
<221> NAME/KEY: misc_feature
<222> LOCATION: (991)..(996)
<220> FEATURE:
<221> NAME/KEY: CDS
<222> LOCATION: (1001)..(1777)
<220> FEATURE:
<221> NAME/KEY: misc_feature

```
<222> LOCATION: (1001)..(1003)
<223> OTHER INFORMATION: ATG start codon
<220> FEATURE:
<221> NAME/KEY: misc_feature
<222> LOCATION: (1778)..(2780)
<223> OTHER INFORMATION: DNA sequence located downstream

<400> SEQUENCE: 3
cccaacggaa aaccagatcc agcaagtttg tcagataggc agcgcaggat tttagaggtt      60
atccgagatg ctgtggtttt gaggggttat ccaccaagca ttagggaaat tggtgatgct     120
gcaggacttc aatccacttc ttccgttgct taccagctta aagagctaga agaagaaggc     180
ttcctgcgca gggaccctaa taagcctcgc gcggtggatg ttcgccacct tccagaaact     240
gaaagccgtt cctccaaggc tgctacacag gcaaagagca aggcccctca ggccggggtc     300
catgatcctg agttagctgg ccagacctca tttgtcccag tggtgggcaa aattgccgct     360
ggtagcccga tcaccgctga gcagaacatc gaagagtact acccactccc cgcagaaatc     420
gtcggagacg gtgacttgtt catgctccag gttgttggcg agtccatgag ggatgctggc     480
atcctcaccg gcgactgggt tgttgttcgt tcccagccgg tcgctgagca gggcgagttc     540
gtcgcggcaa tgattgacgg tgaagccacc gtgaaggaat ccacaagga ttcatctggc      600 atctggctcc tgccacacaa cgatacgttt gccccaattc ctgctgagaa tgcagaaatc     660
atgggcaagg ttgtttccgt gatgcgcaag ctttaagtcg cttttcaggt tcccgccaca     720
gtatgtgttc tcacatatcg tggcgggttt tgctttatat agccacattc gggggtaatc     780
gggcaaataa gttttgctg atctagaaag tgagtttacc tgtgggtttt cgaaaattct     840
gggccggaca atagaaaaac gctgcccggt tttttgatt gactcccgat ttcaccccctc     900 cgccggcaac caaatgaggc ttttgggcgt tggacagtga acaatgggt aagaaattcg     960 gacatattta gtaaattggc tttttgcttt aaggagtgac atg tac gca gag gag    1015
                                              Met Tyr Ala Glu Glu
                                               1               5 cgc cgt cga cag att gcc tca tta acg gca gtt gag gga cgt gta aat    1063
Arg Arg Arg Gln Ile Ala Ser Leu Thr Ala Val Glu Gly Arg Val Asn
         10                  15                  20 gtc aca gaa tta gcg ggc cga ttc gat gtc act gca gag acg att cga    1111
Val Thr Glu Leu Ala Gly Arg Phe Asp Val Thr Ala Glu Thr Ile Arg
     25                  30                  35 cga gac ctt gcg gtg cta gac cgc gag gga att gtt cac cgc gtt cac    1159
Arg Asp Leu Ala Val Leu Asp Arg Glu Gly Ile Val His Arg Val His
 40                  45                  50 ggt ggc gca gta gcc acc caa tct ttc caa acc aca gag ttg agc ttg    1207
Gly Gly Ala Val Ala Thr Gln Ser Phe Gln Thr Thr Glu Leu Ser Leu
55                  60                  65 gat act cgt ttc agg tct gca tcg tca gca aag tac tcc att gcc aag    1255
Asp Thr Arg Phe Arg Ser Ala Ser Ser Ala Lys Tyr Ser Ile Ala Lys
70                  75                  80                  85 gca gcg atg cag ttc ctg ccc gct gag cat gga gga ctg ttc ctc gat    1303
Ala Ala Met Gln Phe Leu Pro Ala Glu His Gly Gly Leu Phe Leu Asp
             90                  95                 100 gcg gga act act gtt act gct ttg gcc gat ctc att tct gag cat cct    1351
Ala Gly Thr Thr Val Thr Ala Leu Ala Asp Leu Ile Ser Glu His Pro
        105                 110                 115 agc tcc aag cag tgg tcg atc gtg acc aac tgc ctc ccc atc gca ctt    1399
Ser Ser Lys Gln Trp Ser Ile Val Thr Asn Cys Leu Pro Ile Ala Leu
    120                 125                 130 aat ctg gcc aac gcc ggg ctt gat gat gtc cag ctg ctt gga gga agc    1447
Asn Leu Ala Asn Ala Gly Leu Asp Asp Val Gln Leu Leu Gly Gly Ser
135                 140                 145
```

```
gtt cgc gcg atc acc cag gct gtt gtg ggt gac act gcg ctt cgt act      1495
Val Arg Ala Ile Thr Gln Ala Val Val Gly Asp Thr Ala Leu Arg Thr
150                 155                 160                 165 ctc gcg ctg atg cgt gcg gat gta gtg ttc atc ggc acc aac gcg ttg      1543
Leu Ala Leu Met Arg Ala Asp Val Val Phe Ile Gly Thr Asn Ala Leu
                170                 175                 180 acg ttg gat cac gga ttg tct acg gcc gat tcc caa gag gct gcc atg      1591
Thr Leu Asp His Gly Leu Ser Thr Ala Asp Ser Gln Glu Ala Ala Met
            185                 190                 195 aaa tct gcg atg atc acc aac gcc cac aag gtg gtg gtg ttg tgt gac      1639
Lys Ser Ala Met Ile Thr Asn Ala His Lys Val Val Val Leu Cys Asp
        200                 205                 210 tcc acc aag atg ggc acc gac tac ctc gtg agc ttt ggc gca atc agc      1687
Ser Thr Lys Met Gly Thr Asp Tyr Leu Val Ser Phe Gly Ala Ile Ser
    215                 220                 225 gat atc gat gtg gtg gtc acc gat gcg ggt gca cca gca agt ttc gtt      1735
Asp Ile Asp Val Val Val Thr Asp Ala Gly Ala Pro Ala Ser Phe Val
230                 235                 240                 245 gag cag ttg cga gaa cgc gat gta gaa gtt gtg att gca gaa              1777
Glu Gln Leu Arg Glu Arg Asp Val Glu Val Val Ile Ala Glu
                250                 255 tgattcttac agtcactgca agtccgtatc tgttgagcac caatgagctt gacggcacca   1837
tcgaaattgg cgaagcaaac aaaatccggc aggtttccac tgttgccggt ggttttggca   1897
ccggtgtggc tgccaccttg ttttatggcg gcaatgaaac ttttgcagtt tttcccgctc   1957
cagaaatctc tcattacatg cgcctggtga cgtttgctgg gttgcctcat gaaattattc   2017
cggtggcagg tcccatcccc atgcatttga ccatgcgtga tgcagagggc aatgagacta   2077
agttcaaaga ctcccccatg cctttggatg tgtcccagtt ggcaattctt cgtgatctag   2137
tggtgcgtcg agccgaagat gccgcgtggg tgttgttggg tggcaatttg ccgtctatcg   2197
cgcctgctgc gtggttttgtg gatgtggtga atcacttcg cttgtaccac cctcatgtga   2257
aggtagctat cgcagcaact ggtgctgcgt tgcgtgcggt tattcgacag cttgcagcta   2317
cgtccccgga tgcgctgatt gtggctgcgg aagaaatcga attgccact ggattagaac    2377
ccaaaacctt gagaggtcca tgggtagagg gagatctctc cccgactgtg gcggcagcgc   2437
gcgctttaat tgatagcggt gtcaccgagg tgttggttac caacaagcgg acggaatctt   2497
tgtatgtttc cgagtctgaa tcactgttag ccagctacga cagcaccccct ggtaagcagg   2557
gcgtgaattg gcgggaatct tttactgcag gattcttggc agcatccaat gatggaaaat   2617
ccactgagga cagcgtgatc aacgcggttg cttacgccaa cgctgaaggc agtgagtggg   2677
acaactacat tcccacaccc gataagcttc gggcggagca cgtggtcatc aaatcgcttt   2737
agaccacgca aaaagcctca aattcccaca caggaatttg agg                    2780
```

<210> SEQ ID NO 4
<211> LENGTH: 259
<212> TYPE: PRT
<213> ORGANISM: Corynebacterium glutamicum

<400> SEQUENCE: 4

```
Met Tyr Ala Glu Glu Arg Arg Gln Ile Ala Ser Leu Thr Ala Val
1               5                   10                  15

Glu Gly Arg Val Asn Val Thr Glu Leu Ala Gly Arg Phe Asp Val Thr
                20                  25                  30

Ala Glu Thr Ile Arg Arg Asp Leu Ala Val Leu Asp Arg Glu Gly Ile
            35                  40                  45
```

```
Val His Arg Val His Gly Gly Ala Ala Thr Gln Ser Phe Gln Thr
 50                  55                  60
Thr Glu Leu Ser Leu Asp Thr Arg Phe Arg Ser Ala Ser Ser Ala Lys
 65                  70                  75                  80
Tyr Ser Ile Ala Lys Ala Ala Met Gln Phe Leu Pro Ala Glu His Gly
                 85                  90                  95
Gly Leu Phe Leu Asp Ala Gly Thr Thr Val Thr Ala Leu Ala Asp Leu
            100                 105                 110
Ile Ser Glu His Pro Ser Ser Lys Gln Trp Ser Ile Val Thr Asn Cys
        115                 120                 125
Leu Pro Ile Ala Leu Asn Leu Ala Asn Ala Gly Leu Asp Asp Val Gln
130                 135                 140
Leu Leu Gly Gly Ser Val Arg Ala Ile Thr Gln Ala Val Val Gly Asp
145                 150                 155                 160
Thr Ala Leu Arg Thr Leu Ala Leu Met Arg Ala Asp Val Val Phe Ile
                165                 170                 175
Gly Thr Asn Ala Leu Thr Leu Asp His Gly Leu Ser Thr Ala Asp Ser
            180                 185                 190
Gln Glu Ala Ala Met Lys Ser Ala Met Ile Thr Asn Ala His Lys Val
        195                 200                 205
Val Val Leu Cys Asp Ser Thr Lys Met Gly Thr Asp Tyr Leu Val Ser
210                 215                 220
Phe Gly Ala Ile Ser Asp Ile Asp Val Val Thr Asp Ala Gly Ala
225                 230                 235                 240
Pro Ala Ser Phe Val Glu Gln Leu Arg Glu Arg Asp Val Glu Val Val
                245                 250                 255
Ile Ala Glu

<210> SEQ ID NO 5
<211> LENGTH: 4052
<212> TYPE: DNA
<213> ORGANISM: Corynebacterium glutamicum
<220> FEATURE:
<221> NAME/KEY: misc_feature
<222> LOCATION: (662)..(684)
<223> OTHER INFORMATION: Binding site of the SugR transcriptional
      regulator
<220> FEATURE:
<221> NAME/KEY: misc_feature
<222> LOCATION: (743)..(743)
<223> OTHER INFORMATION: start of transcription
<220> FEATURE:
<221> NAME/KEY: CDS
<222> LOCATION: (1001)..(3049)

<400> SEQUENCE: 5
atccaagtac ggaatggctg actcctacga cgagcagggt aactacatct tccctgaggg      60
cttcgacgcc gagaccaacg aatggctcga aggcttcgat gagcagcgtc aggcttggga     120
agctcgctac gccgagtccg agcgtcgctt caccgctcac accgctcaga tcgagcgtcg     180
tcgtcagcag gctgaagagg cagctgccga ggctccggcc ggcaactact ccactgattc     240
tgcagaagat gcacctgcag cagaagcagt tgaaagtccc gctggctccc tcgcttccga     300
tgagcagctc gctgctcttc gcgagaagct cgcaggtaac taatagttcc tgcacctctt     360
aagagggctc actgacgttg acagtgaacc ctcccaaaga gtttgctccg cataaacacc     420
ccgcactttt taaccttcac ggtttgggaa gtgcggggtg ttttgttgtg aggcttggtt     480
ttcgtacggt gtggttaagc ttttggcggg cgcttcggcg aaaatacatg ggcctacaac     540
gccgtctaag cgtgaaactg ggggatgggg atacctggaa tcattcgggg acgtgatgcg     600
```

```
gtggagggggt ggtgcgggca taatctgaca gtgtgtccgt tttcattttc aaaaaatgca    660
ggtcggacat attcaaaagt attacctttt tggtttgtct gtattcagct tgttttgggt    720
gggtttccgg cttatcatga tgggtgactt accgcttaat tggaaaaaag tgtgatccac    780
cacaaatcta ttgcggggga gcctgggaaa ctaggtaaaa attttttgcca aattgtgcaa   840 tcgttttcac aacctgagaa tgtcacaaca cattaagtgg taggcgctga ggaatcgaat    900
ccgattcttt ttcggcccaa ttcgtaacgg cgatcctctt aagtggacaa gaaagtctct    960
tgcccgcggg agacagaccc tacgtttaga aggtttgac atg gcg tcc aaa ctg     1015
                                            Met Ala Ser Lys Leu
                                             1               5 acg acg aca tcg caa cat att ctg gaa aac ctt ggt gga cca gac aat    1063
Thr Thr Thr Ser Gln His Ile Leu Glu Asn Leu Gly Gly Pro Asp Asn
             10                  15                  20 att act tcg atg act cac tgt gcg act cgc ctt cgc ttc caa gtg aag    1111
Ile Thr Ser Met Thr His Cys Ala Thr Arg Leu Arg Phe Gln Val Lys
         25                  30                  35 gat caa tcc att gtt gat caa caa gaa att gac tcc gac cca tca gtt    1159
Asp Gln Ser Ile Val Asp Gln Gln Glu Ile Asp Ser Asp Pro Ser Val
     40                  45                  50 ctt ggc gta gta ccc caa gga tcc acc ggt atg cag gtg gtg atg ggt    1207
Leu Gly Val Val Pro Gln Gly Ser Thr Gly Met Gln Val Val Met Gly
 55                  60                  65 gga tct gtt gca aac tat tac caa gaa atc ctc aaa ctt gat gga atg    1255
Gly Ser Val Ala Asn Tyr Tyr Gln Glu Ile Leu Lys Leu Asp Gly Met
 70                  75                  80                  85 aag cac ttc gcc gac ggt gaa gct aca gag agt tca tcc aag aag gaa    1303
Lys His Phe Ala Asp Gly Glu Ala Thr Glu Ser Ser Ser Lys Lys Glu
                 90                  95                 100 tac ggc gga gtc cgt ggc aag tac tcg tgg att gac tac gcc ttc gag    1351
Tyr Gly Gly Val Arg Gly Lys Tyr Ser Trp Ile Asp Tyr Ala Phe Glu
            105                 110                 115 ttc ttg tct gat act ttc cga cca atc ctg tgg gcc ctg ctt ggt gcc    1399
Phe Leu Ser Asp Thr Phe Arg Pro Ile Leu Trp Ala Leu Leu Gly Ala
        120                 125                 130 tca ctg att att acc ttg ttg gtt ctt gcg gat act ttc ggt ttg caa    1447
Ser Leu Ile Ile Thr Leu Leu Val Leu Ala Asp Thr Phe Gly Leu Gln
    135                 140                 145 gac ttc cgc gct cca atg gat gag cag cct gat act tat gta ttc ctg    1495
Asp Phe Arg Ala Pro Met Asp Glu Gln Pro Asp Thr Tyr Val Phe Leu
150                 155                 160                 165 cac tcc atg tgg cgc tcg gtc ttc tac ttc ctg cca att atg gtt ggt    1543
His Ser Met Trp Arg Ser Val Phe Tyr Phe Leu Pro Ile Met Val Gly
                170                 175                 180 gcc acc gca gct cga aag ctc ggc gca aac gag tgg att ggt gca gct    1591
Ala Thr Ala Ala Arg Lys Leu Gly Ala Asn Glu Trp Ile Gly Ala Ala
            185                 190                 195 att cca gcc gca ctt ctt act cca gaa ttc ttg gca ctg ggt tct gcc    1639
Ile Pro Ala Ala Leu Leu Thr Pro Glu Phe Leu Ala Leu Gly Ser Ala
        200                 205                 210 ggc gat acc gtc aca gtc ttt ggc ctg cca atg gtt ctg aat gac tac    1687
Gly Asp Thr Val Thr Val Phe Gly Leu Pro Met Val Leu Asn Asp Tyr
    215                 220                 225 tcc gga cag gta ttc cca ccg ctg att gca gca att ggt ctg tac tgg    1735
Ser Gly Gln Val Phe Pro Pro Leu Ile Ala Ala Ile Gly Leu Tyr Trp
230                 235                 240                 245 gtg gaa aag gga ctg aag aag atc atc cct gaa gca gtc caa atg gtg    1783
Val Glu Lys Gly Leu Lys Lys Ile Ile Pro Glu Ala Val Gln Met Val
                250                 255                 260
```

|  |  |
|---|---|
| ttc gtc cca ttc ttc tcc ctg ctg att atg atc cca gcg acc gca ttc<br>Phe Val Pro Phe Phe Ser Leu Leu Ile Met Ile Pro Ala Thr Ala Phe<br>265 270 275 | 1831 |
| ctg ctt gga cct ttc ggc atc ggt gtt ggt aac gga att tcc aac ctg<br>Leu Leu Gly Pro Phe Gly Ile Gly Val Gly Asn Gly Ile Ser Asn Leu<br>280 285 290 | 1879 |
| ctt gaa gcg att aac aac ttc agc cca ttt att ctt tcc atc gtt atc<br>Leu Glu Ala Ile Asn Asn Phe Ser Pro Phe Ile Leu Ser Ile Val Ile<br>295 300 305 | 1927 |
| cca ttg ctc tac cca ttc ttg gtt cca ctt gga ttg cac tgg cca cta<br>Pro Leu Leu Tyr Pro Phe Leu Val Pro Leu Gly Leu His Trp Pro Leu<br>310 315 320 325 | 1975 |
| aac gcc atc atg atc cag aac atc aac acc ctg ggt tac gac ttc att<br>Asn Ala Ile Met Ile Gln Asn Ile Asn Thr Leu Gly Tyr Asp Phe Ile<br>330 335 340 | 2023 |
| cag gga cca atg ggt gcc tgg aac ttc gcc tgc ttc ggc ctg gtc acc<br>Gln Gly Pro Met Gly Ala Trp Asn Phe Ala Cys Phe Gly Leu Val Thr<br>345 350 355 | 2071 |
| ggc gtg ttc ttg ctc tcc att aag gaa cga aac aag gcc atg cgt cag<br>Gly Val Phe Leu Leu Ser Ile Lys Glu Arg Asn Lys Ala Met Arg Gln<br>360 365 370 | 2119 |
| gtt tcc ctg ggt ggc atg ttg gct ggt ttg ctc ggc ggc att tcc gag<br>Val Ser Leu Gly Gly Met Leu Ala Gly Leu Leu Gly Gly Ile Ser Glu<br>375 380 385 | 2167 |
| cct tcc ctc tac ggt gtt ctg ctc cga ttc aag aag acc tac ttc cgc<br>Pro Ser Leu Tyr Gly Val Leu Leu Arg Phe Lys Lys Thr Tyr Phe Arg<br>390 395 400 405 | 2215 |
| ctc ctg ccg ggt tgt ttg gca ggc ggt atc gtg atg ggc atc ttc gac<br>Leu Leu Pro Gly Cys Leu Ala Gly Gly Ile Val Met Gly Ile Phe Asp<br>410 415 420 | 2263 |
| atc aag gcg tac gct ttc gtg ttc acc tcc ttg ctt acc atc cca gca<br>Ile Lys Ala Tyr Ala Phe Val Phe Thr Ser Leu Leu Thr Ile Pro Ala<br>425 430 435 | 2311 |
| atg gac cca tgg ttg ggc tac acc att ggt atc gca gtt gca ttc ttc<br>Met Asp Pro Trp Leu Gly Tyr Thr Ile Gly Ile Ala Val Ala Phe Phe<br>440 445 450 | 2359 |
| gtt tcc atg ttc ctt gtt ctc gca ctg gac tac cgt tcc aac gaa gag<br>Val Ser Met Phe Leu Val Leu Ala Leu Asp Tyr Arg Ser Asn Glu Glu<br>455 460 465 | 2407 |
| cgc gat gag gca cgt gca aag gtt gct gct gac aag cag gca gaa gaa<br>Arg Asp Glu Ala Arg Ala Lys Val Ala Ala Asp Lys Gln Ala Glu Glu<br>470 475 480 485 | 2455 |
| gat ctg aag gca gaa gct aat gca act cct gca gct cca gta gct gct<br>Asp Leu Lys Ala Glu Ala Asn Ala Thr Pro Ala Ala Pro Val Ala Ala<br>490 495 500 | 2503 |
| gca ggt gcg gga gcc ggt gca ggt gca gga gcc gct gct ggc gct gca<br>Ala Gly Ala Gly Ala Gly Ala Gly Ala Gly Ala Ala Ala Gly Ala Ala<br>505 510 515 | 2551 |
| acc gcc gtg gca gct aag ccg aag ctg gcc gct ggg gaa gta gtg gac<br>Thr Ala Val Ala Ala Lys Pro Lys Leu Ala Ala Gly Glu Val Val Asp<br>520 525 530 | 2599 |
| att gtt tcc cca ctc gaa ggc aag gca att cca ctt tct gaa gta cct<br>Ile Val Ser Pro Leu Glu Gly Lys Ala Ile Pro Leu Ser Glu Val Pro<br>535 540 545 | 2647 |
| gac cca atc ttt gca gca ggc aag ctt gga cca ggc att gca atc caa<br>Asp Pro Ile Phe Ala Ala Gly Lys Leu Gly Pro Gly Ile Ala Ile Gln<br>550 555 560 565 | 2695 |
| cca act gga aac acc gtt gtt gct cca gca gac gct act gtc atc ctt<br>Pro Thr Gly Asn Thr Val Val Ala Pro Ala Asp Ala Thr Val Ile Leu<br>570 575 580 | 2743 |

```
gtc cag aaa tct gga cac gca gtg gca ttg cgc tta gat agc gga gtt    2791
Val Gln Lys Ser Gly His Ala Val Ala Leu Arg Leu Asp Ser Gly Val
        585                 590                 595 gaa atc ctt gtc cac gtt gga ttg gac acc gtg caa ttg ggc ggc gaa    2839
Glu Ile Leu Val His Val Gly Leu Asp Thr Val Gln Leu Gly Gly Glu
600                 605                 610 ggc ttc acc gtt cac gtt gag cgc agg cag caa gtc aag gcg ggg gat    2887
Gly Phe Thr Val His Val Glu Arg Arg Gln Gln Val Lys Ala Gly Asp
    615                 620                 625 cca ctg atc act ttt gac gct gac ttc att cga tcc aag gat cta cct    2935
Pro Leu Ile Thr Phe Asp Ala Asp Phe Ile Arg Ser Lys Asp Leu Pro
630                 635                 640                 645 ttg atc acc cca gtt gtg gtg tct aac gcc gcg aaa ttc ggt gaa att    2983
Leu Ile Thr Pro Val Val Val Ser Asn Ala Ala Lys Phe Gly Glu Ile
            650                 655                 660 gaa ggt att cct gca gat cag gca aat tct tcc acg act gtg atc aag    3031
Glu Gly Ile Pro Ala Asp Gln Ala Asn Ser Ser Thr Thr Val Ile Lys
        665                 670                 675 gtc aac ggc aag aac gag taacctggga tccatgttgc gcattggact           3079
Val Asn Gly Lys Asn Glu
        680 aacaggaggg atcggcagcg gtaaatctac cgttgccgat cttttgtcat ctgaaggatt  3139 tctcatcgtc gacgcggacc aagttgcccg cgatatcgtc gaacccggac aaccggcatt  3199 agcagagcta gctgaagctt ttggccaaga catcttaaaa cccgacggca ctctagaccg  3259 cgcgggatta gcagccaaag catttgtcag cgaagaacaa acagcgctgc tcaatgccat  3319 tacccaccct cgtatcgccg aagagtcagc tcgtcgattc aacgaagccg aagatcaagg  3379 cgccaaagtt gcggtttatg acatgccttt gcttgtagaa aaaggccttg accgcaagat  3439 ggaccttgtc gtcgtagttg atgttgacgt agaggaacgc gtccgcagac ttgtggaaaa  3499 acgtggcctc acagaggacg acgtgcggcg tcgaatcgct tctcaagtgc ccgacgacgt  3559 cagacttaaa gccgctgaca tcgttgtgga caataacggc acgctagagg accttcatgc  3619 tgaagcaagc aagctgattg ctgagattct tagtcgcgtg aattagcact aaaacatcgt  3679 caaagtcgat ctaccaagaa agccctcgga acaatgcaat tacatcagtt ccgagggctt  3739 tttcgtttga gtgctggtga tgaacgagtg atgagcgagg gcagtaccca tttcctcagt  3799 ttcaaccaat cgcggaagta aggggctggg ggattcctca ggatagtttt atcttgaagc  3859 tgggagatcc gtggcttgaa aaggtaactt gacccgttta ctcacaaggg gaaccggatt  3919 acataccaga agattaatac ttgaaagtag ggttaaccgc gctctgatct ggtacttctg  3979 agatagtcag caaatctgat ataggaaaac tccttatcag aggaagtata gattgtgaat  4039 tttgaaggat tac                                                    4052
```

<210> SEQ ID NO 6
<211> LENGTH: 683
<212> TYPE: PRT
<213> ORGANISM: Corynebacterium glutamicum

<400> SEQUENCE: 6

```
Met Ala Ser Lys Leu Thr Thr Thr Ser Gln His Ile Leu Glu Asn Leu
1               5                   10                  15

Gly Gly Pro Asp Asn Ile Thr Ser Met Thr His Cys Ala Thr Arg Leu
            20                  25                  30

Arg Phe Gln Val Lys Asp Gln Ser Ile Val Asp Gln Gln Glu Ile Asp
        35                  40                  45
```

-continued

```
Ser Asp Pro Ser Val Leu Gly Val Pro Gln Gly Ser Thr Gly Met
    50                  55                  60
Gln Val Val Met Gly Gly Ser Val Ala Asn Tyr Tyr Gln Glu Ile Leu
65                  70                  75                  80
Lys Leu Asp Gly Met Lys His Phe Ala Asp Gly Glu Ala Thr Glu Ser
                85                  90                  95
Ser Ser Lys Lys Glu Tyr Gly Val Arg Gly Lys Tyr Ser Trp Ile
            100                 105                 110
Asp Tyr Ala Phe Glu Phe Leu Ser Asp Thr Phe Arg Pro Ile Leu Trp
            115                 120                 125
Ala Leu Leu Gly Ala Ser Leu Ile Ile Thr Leu Val Leu Ala Asp
        130                 135                 140
Thr Phe Gly Leu Gln Asp Phe Arg Ala Pro Met Asp Glu Gln Pro Asp
145                 150                 155                 160
Thr Tyr Val Phe Leu His Ser Met Trp Arg Ser Val Phe Tyr Phe Leu
                165                 170                 175
Pro Ile Met Val Gly Ala Thr Ala Ala Arg Lys Leu Gly Ala Asn Glu
            180                 185                 190
Trp Ile Gly Ala Ala Ile Pro Ala Ala Leu Leu Thr Pro Glu Phe Leu
        195                 200                 205
Ala Leu Gly Ser Ala Gly Asp Thr Val Thr Val Phe Gly Leu Pro Met
    210                 215                 220
Val Leu Asn Asp Tyr Ser Gly Gln Val Phe Pro Pro Leu Ile Ala Ala
225                 230                 235                 240
Ile Gly Leu Tyr Trp Val Glu Lys Gly Leu Lys Lys Ile Ile Pro Glu
                245                 250                 255
Ala Val Gln Met Val Phe Val Pro Phe Phe Ser Leu Leu Ile Met Ile
            260                 265                 270
Pro Ala Thr Ala Phe Leu Leu Gly Pro Phe Gly Ile Gly Val Gly Asn
        275                 280                 285
Gly Ile Ser Asn Leu Leu Glu Ala Ile Asn Asn Phe Ser Pro Phe Ile
    290                 295                 300
Leu Ser Ile Val Ile Pro Leu Leu Tyr Pro Phe Leu Val Pro Leu Gly
305                 310                 315                 320
Leu His Trp Pro Leu Asn Ala Ile Met Ile Gln Asn Ile Asn Thr Leu
                325                 330                 335
Gly Tyr Asp Phe Ile Gln Gly Pro Met Gly Ala Trp Asn Phe Ala Cys
            340                 345                 350
Phe Gly Leu Val Thr Gly Val Phe Leu Leu Ser Ile Lys Glu Arg Asn
        355                 360                 365
Lys Ala Met Arg Gln Val Ser Leu Gly Gly Met Leu Ala Gly Leu Leu
    370                 375                 380
Gly Gly Ile Ser Glu Pro Ser Leu Tyr Gly Val Leu Leu Arg Phe Lys
385                 390                 395                 400
Lys Thr Tyr Phe Arg Leu Leu Pro Gly Cys Leu Ala Gly Ile Val
                405                 410                 415
Met Gly Ile Phe Asp Ile Lys Ala Tyr Ala Phe Val Thr Ser Leu
            420                 425                 430
Leu Thr Ile Pro Ala Met Asp Pro Trp Leu Gly Tyr Thr Ile Gly Ile
        435                 440                 445
Ala Val Ala Phe Phe Val Ser Met Phe Leu Val Leu Ala Leu Asp Tyr
    450                 455                 460
Arg Ser Asn Glu Glu Arg Asp Glu Ala Arg Ala Lys Val Ala Ala Asp
465                 470                 475                 480
```

```
Lys Gln Ala Glu Glu Asp Leu Lys Ala Glu Ala Asn Ala Thr Pro Ala
                485                 490                 495

Ala Pro Val Ala Ala Ala Gly Ala Gly Ala Gly Ala Gly Ala
            500                 505                 510

Ala Ala Gly Ala Ala Thr Ala Val Ala Ala Lys Pro Lys Leu Ala Ala
            515                 520                 525

Gly Glu Val Val Asp Ile Val Ser Pro Leu Glu Gly Lys Ala Ile Pro
530                 535                 540

Leu Ser Glu Val Pro Asp Pro Ile Phe Ala Ala Gly Lys Leu Gly Pro
545                 550                 555                 560

Gly Ile Ala Ile Gln Pro Thr Gly Asn Thr Val Ala Pro Ala Asp
                565                 570                 575

Ala Thr Val Ile Leu Val Gln Lys Ser Gly His Ala Val Ala Leu Arg
            580                 585                 590

Leu Asp Ser Gly Val Glu Ile Leu Val His Val Gly Leu Asp Thr Val
            595                 600                 605

Gln Leu Gly Gly Glu Gly Phe Thr Val His Val Glu Arg Arg Gln Gln
610                 615                 620

Val Lys Ala Gly Asp Pro Leu Ile Thr Phe Asp Ala Asp Phe Ile Arg
625                 630                 635                 640

Ser Lys Asp Leu Pro Leu Ile Thr Pro Val Val Val Ser Asn Ala Ala
                645                 650                 655

Lys Phe Gly Glu Ile Glu Gly Ile Pro Ala Asp Gln Ala Asn Ser Ser
                660                 665                 670

Thr Thr Val Ile Lys Val Asn Gly Lys Asn Glu
                675                 680
```

<210> SEQ ID NO 7
<211> LENGTH: 1266
<212> TYPE: DNA
<213> ORGANISM: Corynebacterium glutamicum
<220> FEATURE:
<221> NAME/KEY: CDS
<222> LOCATION: (1)..(1266)
<223> OTHER INFORMATION: lysC-encoding region

<400> SEQUENCE: 7

```
gtg gcc ctg gtc gta cag aaa tat ggc ggt tcc tcg ctt gag agt gcg      48
Met Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
                20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
            35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
        50                  55                  60 gaa atg gat atg ctc ctg act gct ggt gag cgt att tct aac gct ctc     240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg     288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc     336
Gly Ser Gln Ala Gly Val Leu Thr Thr Glu Arg His Gly Asn Ala Arg
                100                 105                 110
```

```
att gtt gat gtc act cca ggt cgt gtg cgt gaa gca ctc gat gag ggc      384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc      432
Lys Ile Cys Ile Val Ala Gly Phe Gln Gly Val Asn Lys Glu Thr Arg
130                 135                 140 gat gtc acc acg ttg ggt cgt ggt ggt tct gac acc act gca gtt gcg      480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt      528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag      576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc      624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat      672
Ser Lys Ile Leu Val Leu Arg Ser Val Glu Tyr Ala Arg Ala Phe Asn
210                 215                 220 gtg cca ctt cgc gta cgc tcg tct tat agt aat gat ccc ggc act ttg      720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc      768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att      816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat      864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa      912
Ala Glu Ile Asn Ile Asp Met Val Leu Gln Asn Val Ser Ser Val Glu
290                 295                 300 gac ggc acc acc gac atc acc ttc acc tgc cct cgt tcc gac ggc cgc      960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggt gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc taa                                              1266
Ala Gly Thr Gly Arg
            420
```

<210> SEQ ID NO 8
<211> LENGTH: 421
<212> TYPE: PRT
<213> ORGANISM: Corynebacterium glutamicum

<400> SEQUENCE: 8

```
Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
370                 375                 380
```

```
Ile Ser Val Leu Ile Arg Glu Asp Leu Asp Ala Ala Ala Arg Ala
385                 390                 395                 400

Leu His Glu Gln Phe Gln Leu Gly Gly Glu Asp Glu Ala Val Val Tyr
            405                 410                 415

Ala Gly Thr Gly Arg
            420
```

<210> SEQ ID NO 9
<211> LENGTH: 780
<212> TYPE: DNA
<213> ORGANISM: Corynebacterium glutamicum R
<220> FEATURE:
<221> NAME/KEY: CDS
<222> LOCATION: (1)..(777)

<400> SEQUENCE: 9

```
atg tac gca gag gag cgc cgt cga cag att gcc tca tta acg gca gtt    48
Met Tyr Ala Glu Glu Arg Arg Arg Gln Ile Ala Ser Leu Thr Ala Val
1               5                   10                  15 gag gga cgt gta aat gtc aca gaa tta gcg ggc cga ttc gat gtc act    96
Glu Gly Arg Val Asn Val Thr Glu Leu Ala Gly Arg Phe Asp Val Thr
            20                  25                  30 gca gag acg att cga cga gac ctt gcg gtg cta gac cgc gag gga att   144
Ala Glu Thr Ile Arg Arg Asp Leu Ala Val Leu Asp Arg Glu Gly Ile
        35                  40                  45 gtt cac cgc gtt cac ggt ggc gca gta gcc acc caa tct ttc caa acc   192
Val His Arg Val His Gly Gly Ala Val Ala Thr Gln Ser Phe Gln Thr
    50                  55                  60 aca gag ttg agc ttg gat act cgt ttc agg tct gca tcg tca gca aag   240
Thr Glu Leu Ser Leu Asp Thr Arg Phe Arg Ser Ala Ser Ser Ala Lys
65                  70                  75                  80 tac tcc att gcc aag gca gcg atg cag ttc ctg ccc gct gag cat ggc   288
Tyr Ser Ile Ala Lys Ala Ala Met Gln Phe Leu Pro Ala Glu His Gly
                85                  90                  95 gga ctg ttc ctc gat gcg gga act act gtt act gct ttg gcc gat ctc   336
Gly Leu Phe Leu Asp Ala Gly Thr Thr Val Thr Ala Leu Ala Asp Leu
            100                 105                 110 att tct gag cat cct agc gcc aag cag tgg tcg atc gtg acc aac tgc   384
Ile Ser Glu His Pro Ser Ala Lys Gln Trp Ser Ile Val Thr Asn Cys
        115                 120                 125 ctc ccc atc gca ctt aat ctg gcc aac gcc ggg ctt gat gat gtc cag   432
Leu Pro Ile Ala Leu Asn Leu Ala Asn Ala Gly Leu Asp Asp Val Gln
    130                 135                 140 ctg ctt gga gga agc gtt cgc gcg atc acc cag gct gtt gtg ggt gac   480
Leu Leu Gly Gly Ser Val Arg Ala Ile Thr Gln Ala Val Val Gly Asp
145                 150                 155                 160 act gcg ctt cgt act ctc gcg ctg atg cgt gcg gat gta gtg ttc atc   528
Thr Ala Leu Arg Thr Leu Ala Leu Met Arg Ala Asp Val Val Phe Ile
                165                 170                 175 ggc acc aac gcg ttg acg ttg gat cac gga ttg tct acg gcc gat tcc   576
Gly Thr Asn Ala Leu Thr Leu Asp His Gly Leu Ser Thr Ala Asp Ser
            180                 185                 190 caa gag gct gcc atg aaa tct gcg atg atc acc aac gcc cac aag gtg   624
Gln Glu Ala Ala Met Lys Ser Ala Met Ile Thr Asn Ala His Lys Val
        195                 200                 205 gtg gtg ttg tgt gac tcc acc aag atg ggc acc gac tac ctc gtg agc   672
Val Val Leu Cys Asp Ser Thr Lys Met Gly Thr Asp Tyr Leu Val Ser
    210                 215                 220 ttt ggc gca atc agc gat atc gat gtg gtg gtc acc gat gcg ggt gca   720
Phe Gly Ala Ile Ser Asp Ile Asp Val Val Val Thr Asp Ala Gly Ala
225                 230                 235                 240
```

```
cca gca agt ttc gtt gag cag ttg cga gaa cgc gat gta gaa gtt gtg     768
Pro Ala Ser Phe Val Glu Gln Leu Arg Glu Arg Asp Val Glu Val Val
                245                 250                 255 att gca gaa tga                                                      780
Ile Ala Glu
```

<210> SEQ ID NO 10
<211> LENGTH: 259
<212> TYPE: PRT
<213> ORGANISM: Corynebacterium glutamicum R

<400> SEQUENCE: 10

```
Met Tyr Ala Glu Glu Arg Arg Arg Gln Ile Ala Ser Leu Thr Ala Val
1               5                   10                  15

Glu Gly Arg Val Asn Val Thr Glu Leu Ala Gly Arg Phe Asp Val Thr
            20                  25                  30

Ala Glu Thr Ile Arg Arg Asp Leu Ala Val Leu Asp Arg Glu Gly Ile
        35                  40                  45

Val His Arg Val His Gly Gly Ala Val Ala Thr Gln Ser Phe Gln Thr
    50                  55                  60

Thr Glu Leu Ser Leu Asp Thr Arg Phe Arg Ser Ala Ser Ser Ala Lys
65                  70                  75                  80

Tyr Ser Ile Ala Lys Ala Ala Met Gln Phe Leu Pro Ala Glu His Gly
                85                  90                  95

Gly Leu Phe Leu Asp Ala Gly Thr Thr Val Thr Ala Leu Ala Asp Leu
            100                 105                 110

Ile Ser Glu His Pro Ser Ala Lys Gln Trp Ser Ile Val Thr Asn Cys
        115                 120                 125

Leu Pro Ile Ala Leu Asn Leu Ala Asn Ala Gly Leu Asp Asp Val Gln
    130                 135                 140

Leu Leu Gly Gly Ser Val Arg Ala Ile Thr Gln Ala Val Val Gly Asp
145                 150                 155                 160

Thr Ala Leu Arg Thr Leu Ala Leu Met Arg Ala Asp Val Val Phe Ile
                165                 170                 175

Gly Thr Asn Ala Leu Thr Leu Asp His Gly Leu Ser Thr Ala Asp Ser
            180                 185                 190

Gln Glu Ala Ala Met Lys Ser Ala Met Ile Thr Asn Ala His Lys Val
        195                 200                 205

Val Val Leu Cys Asp Ser Thr Lys Met Gly Asp Tyr Leu Val Ser
    210                 215                 220

Phe Gly Ala Ile Ser Asp Ile Asp Val Val Thr Asp Ala Gly Ala
225                 230                 235                 240

Pro Ala Ser Phe Val Glu Gln Leu Arg Glu Arg Asp Val Glu Val Val
                245                 250                 255

Ile Ala Glu
```

<210> SEQ ID NO 11
<211> LENGTH: 780
<212> TYPE: DNA
<213> ORGANISM: Corynebacterium efficiens
<220> FEATURE:
<221> NAME/KEY: CDS
<222> LOCATION: (1)..(777)

<400> SEQUENCE: 11

```
atg tac gca gag gaa cga cgt cgt caa atc gcc tca ttg acg gcg gtt     48
Met Tyr Ala Glu Glu Arg Arg Arg Gln Ile Ala Ser Leu Thr Ala Val
1               5                   10                  15
```

```
gag ggt cgg gtg aat gtc act gag ctg gcg ggg cgg ttc gac gtg aca      96
Glu Gly Arg Val Asn Val Thr Glu Leu Ala Gly Arg Phe Asp Val Thr
         20                  25                  30 gct gag acc atc cgc agg gat ctc gcg gtg ttg gat agg gag ggc atc     144
Ala Glu Thr Ile Arg Arg Asp Leu Ala Val Leu Asp Arg Glu Gly Ile
     35                  40                  45 gtc cac cgc gta cac gga ggc gct gtc gca acc cag tcc ttc cag acc     192
Val His Arg Val His Gly Gly Ala Val Ala Thr Gln Ser Phe Gln Thr
 50                  55                  60 acg gag ctc agc ctg gac acc cgc ttc cgg tcc gcc tca tcc gcc aaa     240
Thr Glu Leu Ser Leu Asp Thr Arg Phe Arg Ser Ala Ser Ser Ala Lys
 65                  70                  75                  80 tac tcc atc gcg aag gct gca atg cag ttt ctg ccc ccg gcg aat ggt     288
Tyr Ser Ile Ala Lys Ala Ala Met Gln Phe Leu Pro Pro Ala Asn Gly
                 85                  90                  95 ggc atg ttc ctc gat gcc gga acc acc gtc acc gct ctg gcg gac ctg     336
Gly Met Phe Leu Asp Ala Gly Thr Thr Val Thr Ala Leu Ala Asp Leu
            100                 105                 110 att gct gaa cac cct aac gcc aaa cac tgg tcg att gtc acc aac tgt     384
Ile Ala Glu His Pro Asn Ala Lys His Trp Ser Ile Val Thr Asn Cys
        115                 120                 125 ctg cct atc gcc ctc agc ctg gct aac gcc ggc ctc gat gag gtt cag     432
Leu Pro Ile Ala Leu Ser Leu Ala Asn Ala Gly Leu Asp Glu Val Gln
130                 135                 140 ctg ttg ggg ggc agc gtg cgt gcg atc acc cag gcg gtg gtg ggt gac     480
Leu Leu Gly Gly Ser Val Arg Ala Ile Thr Gln Ala Val Val Gly Asp
145                 150                 155                 160 acc gcg ctg agg aca ctc gcc ctc atg cgg gcg gat gtt gtg ttc atc     528
Thr Ala Leu Arg Thr Leu Ala Leu Met Arg Ala Asp Val Val Phe Ile
                165                 170                 175 ggt acc aat gcc ctc acg ctg gat cac gga ctc tcc acc gcg gac tcc     576
Gly Thr Asn Ala Leu Thr Leu Asp His Gly Leu Ser Thr Ala Asp Ser
            180                 185                 190 cag gag gcc gcc atg aaa tca gcg atg atc acc aat gct cac aaa gtg     624
Gln Glu Ala Ala Met Lys Ser Ala Met Ile Thr Asn Ala His Lys Val
        195                 200                 205 gtg gtg ctc tgt gac tcc acg aag atg ggc acg gat tac ctg gtc agt     672
Val Val Leu Cys Asp Ser Thr Lys Met Gly Thr Asp Tyr Leu Val Ser
    210                 215                 220 ttc ggc tcc atc gat gat atc gat gtg gtg gtc acc gac tcc ggc gca     720
Phe Gly Ser Ile Asp Asp Ile Asp Val Val Val Thr Asp Ser Gly Ala
225                 230                 235                 240 ccg gag tcc ttc gtg caa cag ttg cgc gaa cgc gat gtt gag gtg gtg     768
Pro Glu Ser Phe Val Gln Gln Leu Arg Glu Arg Asp Val Glu Val Val
                245                 250                 255 atc gcg gaa tga                                                     780
Ile Ala Glu <210> SEQ ID NO 12
<211> LENGTH: 259
<212> TYPE: PRT
<213> ORGANISM: Corynebacterium efficiens

<400> SEQUENCE: 12

Met Tyr Ala Glu Glu Arg Arg Arg Gln Ile Ala Ser Leu Thr Ala Val
1               5                   10                  15

Glu Gly Arg Val Asn Val Thr Glu Leu Ala Gly Arg Phe Asp Val Thr
            20                  25                  30

Ala Glu Thr Ile Arg Arg Asp Leu Ala Val Leu Asp Arg Glu Gly Ile
        35                  40                  45
```

Val His Arg Val His Gly Gly Ala Val Ala Thr Gln Ser Phe Gln Thr
 50                  55                  60

Thr Glu Leu Ser Leu Asp Thr Arg Phe Arg Ser Ala Ser Ser Ala Lys
 65                  70                  75                  80

Tyr Ser Ile Ala Lys Ala Ala Met Gln Phe Leu Pro Pro Ala Asn Gly
                 85                  90                  95

Gly Met Phe Leu Asp Ala Gly Thr Thr Val Thr Ala Leu Ala Asp Leu
                100                 105                 110

Ile Ala Glu His Pro Asn Ala Lys His Trp Ser Ile Val Thr Asn Cys
            115                 120                 125

Leu Pro Ile Ala Leu Ser Leu Ala Asn Ala Gly Leu Asp Glu Val Gln
        130                 135                 140

Leu Leu Gly Gly Ser Val Arg Ala Ile Thr Gln Ala Val Val Gly Asp
145                 150                 155                 160

Thr Ala Leu Arg Thr Leu Ala Leu Met Arg Ala Asp Val Val Phe Ile
                165                 170                 175

Gly Thr Asn Ala Leu Thr Leu Asp His Gly Leu Ser Thr Ala Asp Ser
                180                 185                 190

Gln Glu Ala Ala Met Lys Ser Ala Met Ile Thr Asn Ala His Lys Val
            195                 200                 205

Val Val Leu Cys Asp Ser Thr Lys Met Gly Thr Asp Tyr Leu Val Ser
        210                 215                 220

Phe Gly Ser Ile Asp Asp Ile Asp Val Val Val Thr Asp Ser Gly Ala
225                 230                 235                 240

Pro Glu Ser Phe Val Gln Gln Leu Arg Glu Arg Asp Val Glu Val Val
                245                 250                 255

Ile Ala Glu

<210> SEQ ID NO 13
<211> LENGTH: 61
<212> TYPE: DNA
<213> ORGANISM: Corynebacterium glutamicum
<220> FEATURE:
<221> NAME/KEY: Promotor region
<222> LOCATION: (1)..(61)
<223> OTHER INFORMATION: corresponding to position 940 to 1000 of SEQ ID
      NO:3
<220> FEATURE:
<221> NAME/KEY: misc_feature
<222> LOCATION: (2)..(7)
<220> FEATURE:
<221> NAME/KEY: misc_feature
<222> LOCATION: (52)..(57)

<400> SEQUENCE: 13
agacaatggg taagaaattc ggacatattt agtaaattgg cttttgctt taaggagtga    60 c                                                                  61

<210> SEQ ID NO 14
<211> LENGTH: 28
<212> TYPE: DNA
<213> ORGANISM: Corynebacterium glutamicum
<220> FEATURE:
<221> NAME/KEY: misc_feature
<222> LOCATION: (1)..(28)
<223> OTHER INFORMATION: Primer sugR_A

<400> SEQUENCE: 14
gcgaattcac aaggattcat ctggcatc                                      28

<210> SEQ ID NO 15

```
<211> LENGTH: 39
<212> TYPE: DNA
<213> ORGANISM: Corynebacterium glutamicum
<220> FEATURE:
<221> NAME/KEY: misc_feature
<222> LOCATION: (1)..(39)
<223> OTHER INFORMATION: Primer sugR_B

<400> SEQUENCE: 15
cccatccact aaacttaaac agcgctcctc tgcgtacat                    39

<210> SEQ ID NO 16
<211> LENGTH: 45
<212> TYPE: DNA
<213> ORGANISM: Corynebacterium glutamicum
<220> FEATURE:
<221> NAME/KEY: misc_feature
<222> LOCATION: (1)..(45)
<223> OTHER INFORMATION: Primer sugR_C

<400> SEQUENCE: 16
tgtttaagtt tagtggatgg gcgagaacgc gatgtagaag ttgtg            45

<210> SEQ ID NO 17
<211> LENGTH: 31
<212> TYPE: DNA
<213> ORGANISM: Corynebacterium glutamicum
<220> FEATURE:
<221> NAME/KEY: misc_feature
<222> LOCATION: (1)..(31)
<223> OTHER INFORMATION: Primer sugR_D

<400> SEQUENCE: 17
gcggatccca aattgccacc caacaacacc c                           31

<210> SEQ ID NO 18
<211> LENGTH: 915
<212> TYPE: DNA
<213> ORGANISM: Corynebacterium glutamicum
<220> FEATURE:
<221> NAME/KEY: primer_bind
<222> LOCATION: (1)..(28)
<223> OTHER INFORMATION: Bindingsite for primer sugR_A
<220> FEATURE:
<221> NAME/KEY: primer_bind
<222> LOCATION: (426)..(464)
<223> OTHER INFORMATION: Bindingsite for primer sugR_B
<220> FEATURE:
<221> NAME/KEY: primer_bind
<222> LOCATION: (444)..(488)
<223> OTHER INFORMATION: Bindingsite for primer sugR_C
<220> FEATURE:
<221> NAME/KEY: primer_bind
<222> LOCATION: (885)..(915)
<223> OTHER INFORMATION: Bindingsite for primer sugR_D

<400> SEQUENCE: 18
gcgaattcac aaggattcat ctggcatctg gctcctgcca cacaacgata cgtttgcccc     60
aattcctgct gagaatgcag aaatcatggg caaggttgtt tccgtgatgc gcaagcttta   120
agtcgctttt caggttcccg ccacagtatg tgttctcaca tatcgtggcg ggttttgctt   180
tatatagcca cattcggggg taatcgggca ataagttttt gctgatcta gaaagtgagt    240 ttacctgtgg gttttcgaaa attctgggcc ggacaataga aaaacgctgc ccggtttttt   300
tgattgactc ccgatttcac ccctccgccg gcaaccaaat gaggcttttg ggcgttggac   360
agtgagacaa tgggtaagaa attcggacat atttagtaaa ttggcttttt gctttaagga   420
gtgacatgta cgcagaggag cgctgtttaa gtttagtgga tgggcgagaa cgcgatgtag   480
```

```
aagttgtgat tgcagaatga ttcttacagt cactgcaagt ccgtatctgt tgagcaccaa    540
tgagcttgac ggcaccatcg aaattggcga agcaaacaaa atccggcagg tttccactgt    600
tgccggtggt tttggcaccg gtgtggctgc caccttgttt tatggcggca atgaaacttt    660
tgcagttttt cccgctccag aaatctctca ttacatgcgc ctggtgacgt ttgctgggtt    720
gcctcatgaa attattccgg tggcaggtcc catccccatg catttgacca tgcgtgatgc    780
agagggcaat gagactaagt tcaaagactc ccccatgcct ttggatgtgt cccagttggc    840
aattcttcgt gatctagtgg tgcgtcgagc cgaagatgcc gcgtgggtgt tgttgggtgg    900
caatttggga tccgc                                                    915

<210> SEQ ID NO 19
<211> LENGTH: 23
<212> TYPE: DNA
<213> ORGANISM: Corynebacterium glutamicum
<220> FEATURE:
<221> NAME/KEY: misc_feature
<222> LOCATION: (1)..(23)
<223> OTHER INFORMATION: Primer sugR-k-for

<400> SEQUENCE: 19
gttcgtcgcg gcaatgattg acg                                            23

<210> SEQ ID NO 20
<211> LENGTH: 23
<212> TYPE: DNA
<213> ORGANISM: Corynebacterium glutamicum
<220> FEATURE:
<221> NAME/KEY: misc_feature
<222> LOCATION: (1)..(23)
<223> OTHER INFORMATION: Primer sugR-k-rev

<400> SEQUENCE: 20
ctcaccacat ccacaaacca cgc                                            23
```

US 8,592,177 B2

PROCESS FOR THE FERMENTATIVE PREPARATION OF ORGANIC CHEMICAL COMPOUNDS USING CORYNEFORM BACTERIA IN WHICH THE SUGR GENE IS PRESENT IN ATTENUATED FORM

CROSS REFERENCE TO RELATED APPLICATIONS

The present application is a divisional of U.S. Ser. No. 12/232,610, filed on Sep. 19, 2008 (now U.S. Pat. No. 8,133,174), which claims the benefit of U.S. provisional application 60/960,375 filed on Sep. 27, 2007 and U.S. provisional application 60/996,706 filed on Nov. 30, 2007. These prior applications are hereby incorporated by reference in their entirety.

FIELD OF THE INVENTION

The invention relates to coryneform bacteria which secrete organic chemical compounds and in which the sugR gene is present in attenuated form. It is also directed to processes for the fermentative preparation of organic chemical compounds, where the medium comprises as a carbon source a mixture of one or more of the sugars selected from the group of glucose, fructose and sucrose, and acetic acid.

BACKGROUND OF THE INVENTION

Organic chemical compounds, particularly amino acids, vitamins, hydroxy acids, keto acids, nucleosides and nucleotides, are used in human medicine, in the pharmaceutical industry, in cosmetics, in the food industry and in livestock nutrition. Many of these compounds are prepared by the fermentation of strains of coryneform bacteria, especially *Corynebacterium glutamicum*. These fermentation procedures are continually being improved by measures relating to: fermentation technology (e.g., changes in stirring or the supply of oxygen); the composition of the nutrient medium (e.g., the sugar concentration during the fermentation); the working up of the product formed (e.g., by ion exchange chromatography); or the intrinsic output properties of the microorganism itself.

Methods used for improving the output properties of bacteria may involve mutagenesis, or changes in the selection and choice of mutants. For example, strains may be developed that produce the organic chemical compound and that are resistant to antimetabolites. Methods of recombinant DNA technology have been employed for some years for improving of L-amino acid-producing strains of *Corynebacterium glutamicum*. A summary of various aspects of the genetics, metabolism and biotechnology of *Corynebacterium glutamicum* may be found in Pühler ((chief ed.) (*J. Biotechnol.* 104 (1-3): 1-338 (2003)) and Eggeling, et al. ((editors) *Handbook of Corynebacterium Glutamicum*, CRC Press, Taylor & Francis Group, Boca Raton (2005)).

Nucleotide sequences of the genes or open reading frames (ORF) of *Corynebacterium glutamicum* ATCC13032 form part of the prior art and can be determined, inter alia, from the genomic sequence published by Kalinowski et al. (*J. Biotechnol.* 104:5-25 (2003), Access No. NC_006958)).

Nucleotide sequences of the genes or open reading frames (ORF) of *Corynebacterium glutamicum* R also form part of the prior art and can be determined, inter alia, from the genomic sequence published by Yukawa et al. (*Microbiol.* 153(4):1042-1058 (2007)), Accession No. NC_009342).

The nucleotide sequences of the genes or open reading frames (ORF) of *Corynebacterium efficiens* likewise form part of the art and can be determined, inter alia, from the genomic sequence published by Nishio, et al. (*Genome Res.* 13:1572-1579 (2003), Accession No. NC_004369).

In addition, numerous nucleotide sequences of *Corynebacterium thermoaminogenes* are known.

Despite this plethora of sequence data, there are numerous ORFs for which no clear function has been assignable to date. Glucose or sucrose is mostly used as carbon source for the fermentative preparation of organic chemical compounds with the aid of coryneform bacteria. There is a continuous search for alternative suitable raw materials or raw material mixtures.

It is known that *Corynebacterium glutamicum* can utilize acetic acid as a carbon source. Investigations on the utilization of mixtures of carbon sources, for example mixtures comprising glucose and one or more of the compounds selected from the group of acetic acid, lactate and fructose are described by Cocaign et al. (*Appl. Microbiol. Biotechnol.* 40:526-530 (1993)), Dominguez, et al. (*Appl. Microbiol. Biotechnol.* 47(5):600-603 (1997)), Dominguez, et al. (*Eur. J. Biochem.* 254(1):96-102. (1998)) and Wendisch, et al. (*J. Bacteriol.* 182(11):3088-96 (2000)).

U.S. Pat. No. 4,368,266 describes a process for preparing L-glutamic acid by using acetic acid as a carbon source with the aid of coryneform bacteria having a defect in isocitrate lyase.

U.S. Pat. No. 4,728,610 describes a process for preparing L-glutamic acid by using carbohydrates and acetic acid as carbon source with the aid of coryneform bacteria.

Wendisch et al. (*J. Bacteriol.* 182(11): 3088-96 (2000)) observed a reduced glucose uptake when acetic acid and glucose were metabolized together.

OBJECT OF THE INVENTION

The object addressed by the inventors was to provide novel coryneform bacteria able to utilize mixtures of carbon sources comprising one or more of the sugars selected from the group consisting of glucose, fructose and sucrose and acetic acid for the effective formation and enrichment of organic chemical compounds. A further object directly connected thereto was to provide an improved process for the fermentative preparation of organic chemical compounds, especially amino acids, vitamins, α-keto acids, nucleosides and nucleotides, with the aid of such coryneform bacteria.

BRIEF DESCRIPTION OF THE DRAWINGS

FIG. 1: Map of the plasmid pK19mobsacB_deltasugR.

DESCRIPTION OF THE INVENTION

The invention relates to recombinant coryneform bacteria which secrete organic chemical compounds and in which the sugR gene, which codes for the SugR regulator, is present in attenuated form These bacteria have the ability to utilize one or more of the sugars selected from the group of glucose, fructose and sucrose, and acetic acid as their carbon source.

Coryneform bacteria, preferably of the genus *Corynebacterium*, are used to prepare the bacteria of the invention. Strains derived from the following species are particularly preferred:

*Corynebacterium efficiens* such as, for example, the type strain DSM44549,

*Corynebacterium glutamicum* such as, for example, the type strain ATCC13032 or the strain R, and

*Corynebacterium ammoniagenes* such as, for example, the strain ATCC6871, with very particular preference for the species *Corynebacterium glutamicum*.

Some representatives of the species *Corynebacterium glutamicum* are known in the prior art under other species names. These include for example:

*Corynebacterium acetoacidophilum* ATCC13870
*Corynebacterium lilium* DSM20137
*Corynebacterium melassecola* ATCC 17965
*Brevibacterium flavum* ATCC 14067
*Brevibacterium lactofermentum* ATCC13869 and
*Brevibacterium divaricatum* ATCC 14020.

The term "*Micrococcus glutamicus*" for *Corynebacterium glutamicum* has likewise been used.

Some representatives of the species *Corynebacterium efficiens* have also been referred to in the prior art as *Corynebacterium thermoaminogenes* such as, for example, the strain FERM BP-1539.

The coryneform bacteria employed for attenuation measures have, inter alia, the ability to utilize the sugars glucose, fructose, sucrose and acetic acid singly or together as a carbon source.

The strains of coryneform bacteria (starting strains) employed for attenuation measures preferably already have the capability of producing organic chemical compound(s) that are enriched in the cell or secreted into nutrient medium. The term "produce" refers to processes entailing either enrichment or secretion. In particular, the strains of coryneform bacteria employed have the ability to enrich or to accumulate $\geq$(at least) 0.25 g/l, $\geq$0.5 g/l, $\geq$1.0 g/l, $\geq$1.5 g/l, $\geq$2.0 g/l, $\geq$4 g/l or $\geq$10 g/l of the desired compound in $\leq$(at most) 120 hours, $\leq$96 hours, $\leq$48 hours, $\leq$36 hours, $\leq$24 hours or $\leq$12 hours in the cell or in the nutrient medium. The starting strains are preferably strains which have been prepared by mutagenesis and selection, by recombinant DNA techniques or by a combination of the two methods.

Bacteria according to the invention can also be obtained by first attenuating the sugR gene in a wild strain such as, for example, ATCC13032, and then genetically engineering the bacteria to produce the desired organic chemical compound(s).

It is further advantageous to carry out the attenuation measures on the sugR gene in strains which require acetic acid as a supplement in the nutrient medium. For example, EP 1767 616 A1 describes strains with attenuated pyruvate dehydrogenase which require acetic acid as a source in the medium to prepare L-amino acids.

The term "organic chemical compound" includes amino acids, vitamins, hydroxy acids, keto acids, nucleosides and nucleotides.

The term "amino acids" includes D-amino acids and L-amino acids. Preferred L-amino acids are the proteinogenic amino acids, L-ornithine and L-homoserine. "Proteinogenic amino acids" refers to the amino acids which occur in natural proteins, i.e., in the proteins of microorganisms, plants, animals and humans, and include L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline and, where appropriate, L-seleno-cysteine and L-pyrrolysine. Particularly preferred proteinogenic amino acids are L-lysine, L-isoleucine, L-valine and L-proline. As used herein, the terms "amino acids" or "L-amino acids" includes salts thereof such as, for example, lysine monohydrochloride or lysine sulfate.

L-lysine-producing or -secreting strains of coryneform bacteria include:

*Corynebacterium glutamicum* DM58-1/pDM6 (=DSM4697) described in EP 0 358 940,
*Corynebacterium glutamicum* MH20-22B (=DSM16835) described in Menkel et al. (*Appl. Env. Microbiol.* 55(3): 684-688 (1989)),
*Corynebacterium glutamicum* AHP-3 (=Ferm BP-7382) described in EP 1 108 790,
*Corynebacterium glutamicum* NRRL B-11474 described in U.S. Pat. No. 4,275,157, and
*Corynebacterium thermoaminogenes* AJ12521 (=FERM BP-3304) described in U.S. Pat. No. 5,250,423.

L-valine-producing or -secreting strains of coryneform bacteria include:

*Brevibacterium lactofermentum* FERM BP-1763 described in U.S. Pat. No. 5,188,948,
*Brevibacterium lactofermentum* FERM BP-3007 described in U.S. Pat. No. 5,521,074,
*Corynebacterium glutamicum* FERM BP-3006 described in U.S. Pat. No. 5,521,074, and
*Corynebacterium glutamicum* FERM BP-1764 described in U.S. Pat. No. 5,188,948.

L-isoleucine-producing or -secreting strains of coryneform bacteria include:

*Brevibacterium flavum* FERM BP-355 described in JP 60030693, and
*Corynebacterium glutamicum* FERM BP-456 described in JP 60030693.

L-proline-producing or -secreting strains of coryneform bacteria include:

*Brevibacterium lactofermentum* NRRL B-11421 described in U.S. Pat. No. 4,224,409, and
*Corynebacterium glutamicum* NRRL B-11423 described in U.S. Pat. No. 4,224,409.

L-homoserine-producing or -secreting strains of coryneform bacteria include:

*Micrococcus glutamicus* ATCC 14296 described in U.S. Pat. No. 3,189,526 and
*Micrococcus glutamicus* ATCC 14297 described in U.S. Pat. No. 3,189,526.

Data on the taxonomic classification of strains of these groups of bacteria may be found, inter alia, in Seiler (*J. Gen. Microbiol.* 129:1433-1477 (1983)), Kinoshita (Glutamic Acid Bacteria, pp. 115-142. In: Demain and Solomon (ed), Biology of Industrial Microorganisms. The Benjamin/Cummins Publishing Co., London, UK (1985)), Kämpfer et al. (*Can. J. Microbiol.* 42:989-1005 (1996)), Liebl et al. (*Inter. J. System. Bacteriol.* 41:255-260 (1991)), Fudou, et al. (*Intern. J. System. Evol. Microbiol.* 52:1127-1131 (2002)) and in U.S. Pat. No. 5,250,434.

Strains with the designation "ATCC" can be purchased from the American Type Culture Collection (Manassas, Va., USA). Strains with the designation "DSM" can be purchased from the Deutsche Sammlung von Mikroorganismen and Zellkulturen (DSMZ, Brunswick, Germany). Strains with the designation "NRRL" can be purchased from the Agricultural Research Service Patent Culture Collection (ARS, Peoria, Ill., US). Strains with the designation "FERM" can be purchased from National Institute of Advanced Industrial Science and Technology (AIST Tsukuba Central 6, 1-1-1 Higashi, Tsukuba Ibaraki, Japan).

In the work on coryneform bacteria which led to the present invention, the sugR gene in the chromosome of these bacteria was identified and characterized, and its physiological significance was described (Engels, et al., *J. Bacteriol.* 189: 2955-2966 (2007)). The sugR gene codes for a polypeptide which is referred to as the SugR transcriptional regulator. It is assigned to the DeoR family of transcriptional regulators. The nucleotide sequence of the sugR gene coding for the SugR regulator of the wild type (ATCC13032) of *Corynebacterium glutamicum* ("wild-type gene") is depicted in SEQ ID NO:1 and the amino acid sequence, resulting therefrom is depicted in SEQ ID NO:2 or 4. SEQ ID NO:3 additionally shows the nucleotide sequences located upstream and downstream of the sugR gene. The terms SugR regulator, SugR transcriptional regulator and SugR polypeptide are mutually interchangeable.

The SugR transcriptional regulator represses, in the presence of so-called gluconeogenic carbon sources such as, for example, acetic acid (acetate), pyruvic acid (pyruvate) or citric acid (citrate), the expression of the ptsG, ptsS and ptsF genes. The ptsG gene codes for the glucose-specific component of the phosphotransferase system (PTS) (Handbook of *Corynebacterium glutamicum*, L. Eggeling and M. Bott (Eds.), CRC Press, 2005). SEQ ID NO:5 depicts the nucleotide sequence of the ptsG, including the nucleotide sequences located upstream and downstream, in *Corynebacterium glutamicum* ATCC13032. SEQ ID NO:8 represents the amino acid sequence of the PtsG polypeptide.

The ptsS gene codes for the sucrose-specific component of the phosphotransferase system and the ptsF gene codes for the fructose-specific component of the phosphotransferase system.

It was found in the work leading to the present invention that the SugR transcriptional regulator binds to a polynucleotide or a nucleotide sequence (DNA binding motif) which is located upstream of the coding region of the ptsG gene and includes the nucleotide sequence corresponding to position 662 to 684 of SEQ ID NO:5.

The sugR gene of coryneform bacteria further includes polynucleotides or alleles which code for variants of the SugR polypeptide which bind with substantially the same activity or affinity to a polynucleotide having the nucleotide sequence corresponding to position 662 to 684 of SEQ ID NO:5, such as the SugR polypeptide shown in SEQ ID NO:2. Polynucleotides suitable for such an assay include or possess, for example, the nucleotide sequence from position 618 to 804 of SEQ ID NO:5 or 611 to 684 of SEQ ID NO:5.

The activity or affinity of the SugR polypeptide for binding to a polynucleotide can be determined with the aid of retardation gel electrophoresis. This entails a polypeptide being mixed with a polynucleotide, and the change in mobility of the polypeptide-loaded polynucleotide fragment in an electric field, typically gel electrophoresis, is investigated. This design of experiment is also known among those skilled in the art as band shift assay or gel retardation assay.

The term "with substantially the same activity or affinity" means in this connection that a slowing of the rate of migration of the polynucleotide loaded with the SugR polypeptide occurs with a 50- to 80-fold molar excess, preferably 60- to 80-fold molar excess, and particularly preferably 65- to 70-fold molar excess, of the SugR polypeptide based on the polynucleotide employed, which includes the nucleotide sequence corresponding to position 662 to 683 of SEQ ID NO:5.

Variants of the SugR polypeptide are for example those whose amino acid sequence is at least 90%, preferably at least 95%, particularly preferably at least 98%, and very particularly preferably at least 99% identical to the amino acid sequence of SEQ ID NO:2, with the length of the encoded SugR polypeptide preferably comprising 259 amino acids. Examples of such variants are the SugR polypeptide of *Corynebacterium glutamicum* R depicted in SEQ ID NO:10 and of *Corynebacterium efficiens* depicted in SEQ ID NO:12. The nucleotide sequences of the relevant genes are detailed in SEQ ID NO:9 and 11.

Variants of the SugR polypeptide also include polypeptides comprising one or more conservative amino acid exchanges relative to SEQ ID NO:2, SEQ ID NO:10 or SEQ ID NO:12. Preferably there should be no more than 10 such exchanges, more preferably not more than 5 or 7 such exchanges, and still more preferably not more than 2 or 3 such exchanges.

In the case of aromatic amino acids, mutual exchanges of phenylalanine, tryptophan and tyrosine are referred to as conservative exchanges. In the case of hydrophobic amino acids, mutual exchanges of leucine, isoleucine and valine are referred to as conservative exchanges. In the case of polar amino acids, mutual exchanges of glutamine and asparagine are referred to as conservative exchanges. In the case of basic amino acids, mutual exchanges of arginine, lysine and histidine are referred to as conservative exchanges. In the case of acidic amino acids, mutual exchanges of aspartic acid and glutamic acid are referred to as conservative exchanges. In the case of amino acids comprising hydroxyl groups, mutual exchanges of serine and threonine are referred to as conservative exchanges.

Variants of the SugR polypeptide also include polypeptides which additionally comprise an extension or truncation of at least one (1) amino acid at the N or C terminus of SEQ ID NO:2, 10 or 12. This extension or truncation amounts to not more than 20, 15, 10, 7, 5, 3 or 2 amino acids or amino acid residues. Such variants include, inter alia, those in which histidine molecules, for example ten histidines, have been attached at the N terminus (histidine tag).

Variants of the SugR polypeptide also include polypeptides in which at least one (1) amino acid is inserted into or deleted from the amino acid sequence of SEQ ID NO:2, 10 or 12. The maximum number of such changes, referred to as "indels," may be 2, 3, 4, or 5 but in no case more than 6 amino acids.

The term "attenuation" designates, in general, the reduction or elimination of the intracellular activity or concentration of one or more enzymes or proteins which are encoded by the corresponding DNA in a microorganism. Attenuation may result from, for example, using a weaker promoter than in the non-recombinant microorganism or parent strain for the corresponding enzyme or protein, using a gene or allele which codes for a corresponding enzyme or protein having a low activity, inactivating the corresponding enzyme or protein or the open reading frame of the gene, and, where appropriate, combining these measures.

"Open reading frame" (ORF) designates a nucleotide sequence segment which may code for a protein, polypeptide or ribonucleic acid, to which no function can be assigned based upon the prior art. After a function has been assigned to the relevant segment of the nucleotide sequence, reference is generally made to a gene. The term "alleles" mean, in general, alternative forms of a given gene. The forms are distinguished by differences in the nucleotide sequence.

The polypeptide or protein encoded by a gene or an allele, or the encoded ribonucleic acid, is referred to as a "gene product." The terms "protein" and "polypeptide" are used as synonyms herein. It is known that the terminal methionine is deleted during protein synthesis by enzymes intrinsic to the host, called amino peptidases.

A review of known promoters of varying strengths in *Corynebacterium glutamicum* may be found in Pátek et al. (*J. Biotechnol.* 104:311-323 (2003)). Further weak promoters are described in communication 512057 of the periodical "Research Disclosure" of December 2006 (pages 1616 to 1618).

Mutations suitable for attenuating genes include transitions, transversions, insertions and deletions of at least one (1) base pair or nucleotide in the coding region of the relevant gene. Missense mutations lead to an exchange of a given amino acid in a protein for non-conservative amino acid. As a result, the function or activity of the protein is impaired and reduced to a value of from 0 to 75%, 0 to 50%, 0 to 25%, 0 to 10% or 0 to 5%. Nonsense mutations lead to a stop codon in the coding region of the gene and thus to premature termination of translation (switching off).

Insertions or deletions of at least one base pair in a gene lead to frame shift mutations which result in incorrect amino acids being incorporated or translation being prematurely terminated. If the mutation results in a stop codon in the coding region, this likewise leads to premature termination of translation. The measures used to generate a nonsense mutation are preferably carried out in the 5'-terminal part of genes, which codes for the N terminus of the polypeptide. If the total length of a polypeptide (measured as number of chemically connected L-amino acids) is designated at 100%, the N terminus of the polypeptide includes—in the context of the present invention—the part of the amino acid sequence which, calculated from the L-formylmethionine starting amino acid, comprises 80% of the subsequent L-amino acids.

In vivo mutagenesis methods are described, for example, in the Manual of Methods for General Bacteriology (Gerhard et al. (eds.), American Society for Microbiology, Washington, D.C., USA, 1981) or in Tosaka et al. (*Agri. Biol. Chem.* 42(4):745-752 (1978)) or in Konicek, et al. (*Folia Microbiologica* 33:337-343 (1988)). Suitable methods for in vitro mutagenesis include treatment with hydroxylamine as disclosed by Miller (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992), the use of mutagenic oligonucleotides (Brown: Gentechnologie für Einsteiger, Spektrum Akademischer Verlag, Heidelberg, 1993 and Horton, *Mol. Biotech.* 3:93-99 (1995)) and the use of a polymerase chain reaction employing a DNA polymerase which shows a high error rate. One example of such a DNA polymerase is the Mutazyme DNA polymerase (GeneMorph PCR Mutagenesis Kit, No. 600550) supplied by Stratagene (LaJolla, Calif., USA).

Further instructions and reviews on the generation of mutations in vivo or in vitro can be found in the prior art and known textbooks of genetics and molecular biology such as, for example, the textbook of Knippers ("Molekulare Genetik", 6th edition, Georg Thieme Verlag, Stuttgart, Germany, 1995), that of Winnacker ("Gene and Klone", VCH Verlagsgesellschaft, Weinheim, Germany, 1990) or that of Hagemann ("Allgemeine Genetik", Gustav Fischer Verlag, Stuttgart, 1986).

The method of gene or allele exchange, which is described in principle in Schwarzer and Pühler (*Bio/Technology* 9:84-87 (1991)) can be used to transfer a mutation produced in vitro, or a polynucleotide comprising the desired mutation, into the chromosome. Schäfer et al. (*Gene* 145:69-73 (1994)) employed this method to incorporate a deletion into the hom-thrB operon of *C. glutamicum*. Nakagawa et al. (EP 1108790) and Ohnishi et al. (Appl. *Microbiol. Biotechnol.* 58(2):217-223 (2002)) employed this method to incorporate various mutations starting from the isolated alleles into the chromosome of *C. glutamicum*.

One method for targeted reduction of gene expression consists of placing the gene to be attenuated under the control of a promoter which can be induced by addition of metered amounts of IPTG (isopropyl β-D-thiogalactopyranoside), such as, for example, the trc promoter or the tac promoter. Vectors that may be used for this purpose include, for example, the *Escherichia coli* expression vector pXK99E (WO0226787; deposited in accordance with the Budapest Treaty on 31 Jul. 2001 in DH5alpha/pXK99E as DSM14440 at the Deutsche Sammlung für Mikroorganismen and Zellkulturen (DSMZ, Brunswick, Germany)), pEKEx2 (NCBI Accession No. AY585307) or PVWEx2 (Wendisch, Ph. D. thesis, Berichte des Forschungszentrums Jülich, Jül-3397, ISSN 0994-2952, Jülich, Germany (1997)), which make IPTG-dependent expression of the cloned gene possible in *Corynebacterium glutamicum*. This method has been employed, for example, in WO0226787 for the regulated expression of the deaD gene by integration of the vector pXK99EdeaD into the genome of *Corynebacterium glutamicum* and by Simic, et al. (*Appl. Environ. Microbiol.* 68:3321-3327 (2002)) for the regulated expression of the glyA gene by integration of the vector pK18mobglyA' into *Corynebacterium glutamicum*.

A further method for specifically reducing gene expression is the antisense technique, in which short oligodeoxynucleotides or vectors are brought into target cells to synthesize longer antisense RNA. The antisense RNA is able to bind there to complementary segments of specific mRNAs and reduce their stability, or block translatability. One example thereof is to be found by the skilled person in Srivastava, et al. (*Appl. Environ. Microbiol.* 66(10):4366-4371 (2000)).

The rate of elongation is influenced by the codon used, and it is possible to use codons for t-RNAs that occur rarely in the parent strain to attenuate gene expression. It is also possible to exchange an ATG start codon for a less commonly occurring GTG or TTG codon to impair translation. In this regard, it should be noted that the AUG codon is two to three times more efficient than the GUG and UUG codons (Khudyakov et al., *FEBS Letters* 232(2):369-71 (1988); Reddy et al., *Proc. Nat'l Acad. Sci. USA* 82 (17):5656-60 (1985)).

Attenuated forms of the sugR gene or of other genes can be detected with the aid of 1- and 2-dimensional protein gel fractionation and subsequent visual identification of the protein concentration in the gel with appropriate evaluation software. A useful method for preparing the protein gels in the case of coryneform bacteria and for identifying the proteins is the procedure described by Hermann, et al. (*Electrophoresis*, 22:1712-23 (2001)). The protein concentration can likewise be analyzed by Western blot hybridization with an antibody specific for the protein to be detected (Sambrook, et al., Molecular cloning: a laboratory manual. 2nd Ed. Cold Spring Harbor Laboratory Press, Cold Spring Harbor, N.Y., 1989) and subsequent visual evaluation with appropriate software to determine concentration (Lohaus et al., *Biospektrum* 5:32-39 (1998); Lottspeich, *Angewandte Chemie* 111:2630-2647 (1999)).

The activity of DNA-binding proteins can be measured by means of a DNA band shift assay (also referred to as gel retardation) (Wilson, et al., *J. Bacteriol.* 183:2151-2155 (2001)). The effect of DNA-binding proteins on the expression of other genes can be detected by various well-described reporter gene assay methods (Sambrook et al., Molecular cloning: a laboratory manual. 2nd Ed. Cold Spring Harbor Laboratory Press, Cold Spring Harbor, N.Y., 1989). The intracellular enzymatic activities can be determined by various described methods (Donahue, et al., *J. Bacteriol.* 182 (19):5624-5627 (2000); Ray, et al., *J. Bacteriol.* 182(8):2277-2284 (2000); Treedburg, et al., *J. Bacteriol.* 115(3):816-823 (1973)).

Attenuation measures generally reduce the activity or concentration of the corresponding protein to 0 to 75%, 0 to 50%, 0 to 25%, 0 to 10% or 0 to 5% of the activity or concentration of the wild-type protein, or of the activity or concentration of the protein in the non-recombinant microorganism or parent strain for the corresponding enzyme or protein. "Non-recombinant microorganism" or "parent strain" means the microorganism on which attenuation measures are carried out.

The invention preferably relates to a recombinant coryneform bacterium which produces an organic chemical compound and in which the sugR gene which codes for an SugR regulator or SugR polypeptide has been attenuated. Prior to attenuation, the SugR regulator has an amino acid sequence corresponding to that described above.

The SugR regulator preferably includes or possesses an amino acid sequence from the group consisting of:
 a) amino acid sequence of SEQ ID NO:2, 10 or 12 including one or more conservative amino acid exchanges, and preferably the amino acid sequence of SEQ ID NO:2 including one or more conservative amino acid exchanges and
 b) amino acid sequence of SEQ ID NO:2, 10 or 12, preferably the amino acid sequence of SEQ ID NO:2.

The invention preferably relates to coryneform bacteria in which the attenuation of expression of the sugR gene is achieved by one or more of the measures selected from the group of
 a) replacement of the nucleobase thymine at position 946 of SEQ ID NO:3 by guanine,
 b) deletion of one or more of the nucleobases from position 941 to 946, preferably deletion of all nucleobases from position 941 to 946, of SEQ ID NO:3,
 c) deletion of one or more of the nucleobases between position 991 and 996 of SEQ ID NO:3,
 d) replacement of one or more of the nucleobases adenine or guanine between position 991 and 996 of SEQ ID NO:3 by thymine or cytosine.
 e) exchange of the ATG start codon at position 1 to 3 of SEQ ID NO: 1 for a GTG or TTG.

The promoter region of the sugR gene is shown in SEQ ID NO:13. Position 1 of SEQ ID NO: 13 corresponds to position 940 of SEQ ID NO: 3. Positions 2, 7, 52 and 57 of SEQ ID NO:13 are in accordance with positions 941, 946, 991 and 996 of SEQ ID NO:3. Directly connected to the 3' end of the promoter region is the coding region of the sugR gene (or variant of the sugR gene), as for instance shown in SEQ ID NO:3.

The invention preferably relates to coryneform bacteria in which the attenuation of expression of the sugR gene is achieved by one or more of the measures selected from the group of
 a) replacement of the nucleobase thymine at position 7 of SEQ ID NO:13 by guanine,
 b) deletion of one or more of the nucleobases from position 2 to 7, preferably deletion of all nucleobases from position 2 to 7, of SEQ ID NO:13,
 c) deletion of one or more of the nucleobases between position 52 and 57 of SEQ ID NO:13,
 d) replacement of one or more of the nucleobases adenine or guanine between position 52 and 57 of SEQ ID NO:13 by thymine or cytosine.

The invention further relates preferably to coryneform bacteria in which the attenuation of the sugR gene is achieved by one or more of the measures of amino acid exchange selected from the group of
 a) exchange of L-arginine at position 37 of SEQ ID NO:2, 10 or 12, preferably SEQ ID NO:2, for an amino acid selected from the group of L-alanine, glycine, L-isoleucine and L-proline, preferably L-proline,
 b) exchange of L-arginine at position 38 of SEQ ID NO:2, 10 or 12, preferably SEQ ID NO:2, for an amino acid selected from the group of L-alanine, glycine, L-isoleucine and L-proline, preferably L-proline,
 c) exchange of L-aspartic acid at position 39 of SEQ ID NO:2, 10 or 12, preferably SEQ ID NO:2, for an amino acid selected from the group of L-alanine, glycine, L-isoleucine and L-proline, preferably L-proline,
 d) exchange of L-leucine at position 40 of SEQ ID NO:2, 10 or 12, preferably SEQ ID NO:2, for L-proline,
 e) exchange of L-arginine at position 72 of SEQ ID NO:2, 10 or 12, preferably SEQ ID NO:2, for an amino acid selected from the group of L-alanine, glycine, L-glutamic acid and L-aspartic acid, preferably L-alanine,
 f) exchange of L-aspartic acid at position 101 of SEQ ID NO:2, 10 or 12, preferably SEQ ID NO:2, for an amino acid selected from the group of L-arginine, L-lysine, L-phenylalanine, L-methionine, L-glutamine, L-tryptophan, L-tyrosine and L-glutamic acid, preferably L-arginine,
 g) exchange of L-threonine at position 105 of SEQ ID NO:2, 10 or 12, preferably SEQ ID NO:2, for an amino acid selected from the group of L-proline, L-phenylalanine, L-isoleucine, L-methionine, L-glutamine, L-tryptophan and L-tyrosine, preferably L-proline,
 h) exchange of L-valine at position 210 of SEQ ID NO:2, 10 or 12, preferably SEQ ID NO:2, for an amino acid selected from the group of L-alanine, L-arginine, and L-proline, preferably L-alanine, and
 i) exchange of L-lysine at position 216 of SEQ ID NO:2, 10 or 12, preferably SEQ ID NO:2, for an amino acid sequence selected from the group of L-alanine, L-glutamic acid, L-isoleucine and L-tryptophan, preferably L-alanine.

The stated measures of amino acid exchange in the polypeptide shown in SEQ ID NO:2, 10 or 12, preferably SEQ ID NO:2, can be combined with one or more measures of deletion or replacement of nucleotides at positions 946, 941 to 946, 991 to 996 of SEQ ID NO:3 and positions 1 to 3 of SEQ ID NO:2, as stated above.

The invention finally relates to coryneform bacteria in which the switching off of the sugR gene is achieved by a mutagenesis within the coding region of the sugR gene selected from the group of
 a) insertion of one or more nucleobases,
 b) deletion of one or more nucleobases,
 c) deletion of one or more codons, and
 d) transversion or transition of one or more nucleobase(s) which leads to at least one stop codon,
where the mutagenesis measure for switching off preferably takes place within the nucleotide sequence which codes for the amino acids from position 1 to 230, preferably from position 6 to 58, of SEQ ID NO:2, 10 or 12. A deletion is a preferred measure, with particular preference for a deletion of the nucleotide sequence which codes for the amino acids from position 7 to 248 or 1 to 259 of SEQ ID NO:2, 10 or 12.

L-Lysine-producing coryneform bacteria typically have a feedback-resistant or desensitized aspartate kinase. Feedback-resistant aspartate kinases mean aspartate kinases (LysC) which, in comparison with the wild form, exhibit less sensitivity to inhibition by mixtures of lysine and threonine or mixtures of AEC (aminoethylcysteine) and threonine or lysine alone or AEC alone. The genes or alleles coding for these desensitized aspartate kinases are also referred to as lysC$^{FBR}$ alleles. Numerous lysC$^{FBR}$ alleles are described in the state of the art and code for aspartate kinase variants which have amino acid exchanges by comparison with the wild-type protein. The coding region of the wild-type lysC gene of *Corynebacterium glutamicum* corresponding to the access number AX756575 of the NCBI database is depicted in SEQ ID NO:7, and the polypeptide encoded by this gene is depicted in SEQ ID NO:8.

The L-lysine-producing coryneform bacteria used for the invention preferably have a lysC allele which codes for a feedback-resistant aspartate kinase. Particularly preferred aspartate kinase variants have the amino acid sequence of SEQ ID NO:8, the latter including one or more of the amino acid exchanges selected from the group:

LysC A279T (L-alanine at position 279 of the encoded aspartate kinase protein according to SEQ ID NO:8 exchanged for L-threonine; see U.S. Pat. No. 5,688,671 and access numbers E06825, E06826, E08178 and I74588 to I74597), LysC A279V (L-alanine at position 279 of the encoded aspartate kinase protein according to SEQ ID NO:8 exchanged for L-valine, see JP 6-261766 and access number E08179), LysC L297Q (L-leucine at position 297 of the encoded aspartate kinase protein according to SEQ ID NO:8 exchanged for L-glutamine; see DE 102006026328), LysC S301F (L-serine at position 301 of the encoded aspartate kinase protein according to SEQ ID NO:8 exchanged for L-phenylalanine; see U.S. Pat. No. 6,844, 176 and access number E08180), LysC S301Y (L-serine at position 301 of the encoded aspartate kinase protein according to SEQ ID NO:8 exchanged for L-tyrosine, see Kalinowski, et al. (*Mol. Gen. Genet.* 224:317-324 (1990)) and access number X57226), LysC T308I (L-threonine at position 308 of the encoded aspartate kinase protein according to SEQ ID NO:8 exchanged for L-isoleucine; see JP 6-261766 and access number E08181)

LysC T311I (L-threonine at position 311 of the encoded aspartate kinase protein according to SEQ ID NO:8 exchanged for L-isoleucine; see WO 00/63388 and U.S. Pat. No. 6,893,848), LysC S317A (L-serine at position 317 of the encoded aspartate kinase protein according to SEQ ID NO:12 exchanged for L-alanine; see U.S. Pat. No. 5,688,671 and access number 174589), LysC R320G (L-arginine at position 320 of the encoded aspartate kinase protein according to SEQ ID NO:8 exchanged for glycine; see Jetten et al. (*Appl. Microbiol. Biotechnol.* 43:76-82 (1995)) and access number L27125), LysC G345D (glycine at position 345 of the encoded aspartate kinase protein according to SEQ ID NO:8 exchanged for L-aspartic acid; see Jetten, et al. (*Appl. Microbiol. Biotechnol.* 43:76-82 (1995)) and access number L16848), LysC T380I (L-threonine at position 380 of the encoded aspartate kinase protein according to SEQ ID NO:8 exchanged for L-isoleucine; see WO 01/49854 and access number AX192358), and LysC S381F (L-serine at position 381 of the encoded aspartate kinase protein according to SEQ ID NO:8 exchanged for L-phenylalanine; see EP 0435132).

The aspartate kinase variants may additionally comprise, where appropriate, the exchange LysC S317A (L-serine at position 317 of the encoded aspartate kinase protein according to SEQ ID NO:8 exchanged for L-alanine; see U.S. Pat. No. 5,688,671 and access number 174589).

Particular preference is given among the aspartate kinase variants to the variants LysC T311I (threonine at position 311 of the encoded aspartate kinase protein according to SEQ ID NO:8 exchanged for isoleucine) and the variants comprising at least one exchange selected from the group of A279T (alanine at position 279 of the encoded aspartate kinase protein according to SEQ ID NO:8 exchanged for threonine), S381F (serine at position 381 of the encoded aspartate kinase protein according to SEQ ID NO:8 exchanged for phenylalanine) and T380I (L-threonine at position 380 of the encoded aspartate kinase protein according to SEQ ID NO:8 exchanged for L-isoleucine). The lysC T311I variant (threonine at position 311 of the encoded aspartate kinase protein according to SEQ ID NO:8 exchanged for isoleucine) is very particularly preferred. The strain DSM 16833 (WO 06/063660) has a lysC$^{FBR}$ allele which codes for an aspartate kinase protein which comprises the amino acid exchange T311I. The strain NRRL B-11474 (U.S. Pat. No. 4,275,157) has a lysC$^{FBR}$ allele which codes for an aspartate kinase protein which comprises the amino acid exchange S381F. It has further emerged that it is advantageous for lysine production to overexpress the lysC$^{FBR}$ alleles.

In a further embodiment, the coryneform bacteria employed for the measures of L-lysine production, which preferably additionally comprise a polynucleotide which codes for a lysine-insensitive aspartate kinase variant, have one or more of the features selected from the group:

a) overexpressed polynucleotide (asd gene) which codes for an aspartate-semialdehyde dehydrogenase (Asd),
b) overexpressed polynucleotide (dapA gene) which codes for a dihydrodipicolinate synthase (DapA),
c) overexpressed polynucleotide (dapB gene) which codes for a dihydropicolinate reductase (DapB),
d) overexpressed polynucleotide (dapD gene) which codes for a tetrahydrodipicolinate succinylase (DapD),
e) overexpressed polynucleotide (dapC gene) which codes for a succinyl-aminoketopimelate transaminase (DapC),
f) overexpressed polynucleotide (dapE) which codes for a succinyl-diaminopimelate desuccinylase (DapE),
g) overexpressed polynucleotide (ddh gene) which codes for a diaminopimelate dehydrogenase (Ddh),
h) overexpressed polynucleotide (dapF gene) which codes for a diaminopimelate epimerase (DapF),
i) overexpressed polynucleotide (lysA gene) which codes for a diaminopimelate decarboxylase (LysA),
j) overexpressed polynucleotide (lysE gene) which codes for a polypeptide having L-lysine export activity (LysE),
k) overexpressed polynucleotide (aat gene) which codes for an aspartate aminotransferase (Aat),
l) overexpressed polynucleotide (pyc gene) which codes for a pyruvate carboxylase (Pyc),
m) eliminated or attenuated activity of the malate-quinone oxidoreductase (Mqo), encoded by the mqo gene,
n) eliminated or attenuated activity of the malate dehydrogenase (Mdh) encoded by the mdh gene,
o) eliminated or attenuated activity of the citrate synthase (GltA) encoded by the gltA gene.

Genes known in the prior art can be used for overexpression of the stated genes or polynucleotides, for example the so-called wild-type genes of *Escherichia coli* (Blattner et al., *Science* 277(5):1453-1462 (1997)), *Bacillus subtilis* (Kunst, et al, *Nature* 390:249-256 (1977)), *Bacillus licheniformis* (Veith et al, *J. Mol. Microbiol. Biotechnol.* 7(4):204-211 (2004)), *Mycobacterium tuberculosis* (Fleischmann et al, *J. Bacteriol.* 1841:5479-5490 (2004)), *Mycobacterium bovis* (Garnier et al, *Proc. Nat'l Acad. Sci. USA.* 100 (13):7877-7882 (2003)), *Streptomyces coelicolor* (Redenbach, et al,

*Mol. Microbiol.* 21(1):77-96 (1996)), *Lactobacillus acidophilus* (Altermann et al, *Proc. Nat'l Acad. Sci. USA* 102(11): 3906-3912 (2005)), *Lactobacillus johnsonii* (Pridmore, et al, *Proc. Nat'l Acad. Sci. USA* 101(8):2512-2517 (2004)), *Bifidobacterium longum* (Schell, et al, *Proc. Nat'l Acad. Sci. USA* 99(22):14422-14427 (2002)), and *Saccharomyces cerevisiae*. The genomes of the wild-type forms of these bacteria are available in sequenced and annotated form. The endogenous genes or polynucleotides of the genum *Corynebacterium*, particularly preferably of the species *Corynebacterium glutamicum*, are preferably used.

The nucleic acid sequences can be taken from the databases of the National Center for Biotechnology Information (NCBI) of the National Library of Medicine (Bethesda, Md., USA), the nucleotide sequence database of the European Molecular Biologies Laboratories (EMBL, Heidelberg, Germany and Cambridge, UK) or the DNA database of Japan (DDBJ, Mishima, Japan).

Endogenous genes and polynucleotides mean respectively the open reading frames (ORF), genes or alleles, and polynucleotides thereof, present in the population of a species. The dapA gene of *Corynebacterium glutamicum* ATCC13032 strain is described for example in EP 0 197 335. It is additionally possible to employ for overexpression of the dapA gene of *Corynebacterium glutamicum*, inter alia, the mutations MC20 and MA16 as described in U.S. Pat. No. 6,861,246. EC No. 4.2.1.52 is assigned to dihydrodipicolinate synthase activity.

The asd gene of *Corynebacterium glutamicum* ATCC 21529 strain is described for example in U.S. Pat. No. 6,927, 046. EC No. 1.2.1.11 is assigned to aspartate-semialdehyde dehydrogenase activity.

The lysA gene of *Corynebacterium glutamicum* ATCC13869 (*Brevibacterium lactofermentum*) is described for example in U.S. Pat. No. 6,090,597. EC No. 4.1.1.20 is assigned to diaminopimelate decarboxylase activity.

The aat gene of *Corynebacterium glutamicum* ATCC13032 is described for example in Kalinowski, et al (*J. Biotechnol.* 104(1-3):5-25 (2003); see also access number NC_006958). It is referred to therein as aspB gene. A gene coding for an aspartate aminotransferase is referred to as aspC in U.S. Pat. No. 6,004,773. Marienhagen, et al (*J. Bacteriol.* 187(22):7693-7646 (2005) refer to the aat gene as aspT gene. EC No. 2.6.1.1 is assigned to aspartate aminotransferase activity.

The lysE gene of *Corynebacterium glutamicum* R127 is described for example in U.S. Pat. No. 6,858,406. The R127 strain is a restriction-defective mutant of ATCC13032 (Liebl, et al, *FEMS Microbiol. Lett.* 65:299-304 (1989)). The lysE gene of the ATCC13032 strain used in U.S. Pat. No. 6,861, 246 can be employed in the same way.

The pyc gene of *Corynebacterium glutamicum* of the ATCC 13032 strain is described for example in WO 99/18228 and WO 00/39305. It is further possible to use alleles of the pyc gene as are described for example in U.S. Pat. No. 6,965, 021. The pyruvate carboxylases described in this patent have one or more of the amino acid exchanges selected from the group: Pyc E153D (L-glutamic acid at position 153 exchanged for L-aspartic acid), Pyc A182S (L-alanine at position 182 exchanged for L-serine), Pyc A206S (L-alanine at position 206 exchanged for L-serine), Pyc H227R (L-histidine at position 227 exchanged for L-arginine), Pyc A455G (L-alanine at position 455 exchanged for glycine), and Pyc D1120E (L-aspartic acid at position 1120 exchanged for L-glutamic acid). The pyc allele which codes for a pyruvate carboxylase which comprises the amino acid exchange Pyc P458S (L-proline at position 458 exchanged for L-serine), and which is described in EP 1 108 790 can be used in the same way. EC No. 6.4.1.1 is assigned to pyruvate carboxylase.

The ddh gene of *Corynebacterium glutamicum* ATCC 13869 strain is described for example in U.S. Pat. No. 6,090, 597. EC No. 1.4.1.16 is assigned to meso-diaminopimelate dehydrogenase.

Genetic measures for eliminating malate-quinone oxidoreductase (Mqo) are described for example in U.S. Pat. No. 7,094,106. EC No. 1.1.99.16 is assigned to malate-quinone oxidoreductase.

Genetic measures for eliminating malate dehydrogenase (Mdh) are described for example in WO 02/02778. EC No. 1.1.1.37 is assigned to malate dehydrogenase.

It is likewise possible by suitable amino acid exchanges to reduce the catalytic property of the relevant polypeptide. In the case of malate-quinone oxidoreductase (Mqo) this can be achieved, as described in WO 06/077004, by producing and using alleles of the mqo gene which code for an Mqo variant which has the amino acid sequence as described in WO 06/077004 and comprises one or more amino acid exchanges selected from the group of
  a) L-serine at position 111 exchanged for another proteinogenic amino acid, preferably L-phenylalanine or L-alanine, and
  b) L-alanine at position 201 exchanged for another proteinogenic amino acid, preferably L-serine.

Particularly preferred strains comprise an mqo allele which codes for an Mqo variant which comprises L-phenylalanine at position 111.

In the case of citrate synthase (GltA), a reduction in catalytic properties can be achieved, as described in PCT/EP2007/056153, by producing and using alleles of the gltA gene which code for a GltA variant which has the amino acid sequence as described in PCT/EP2007/056153, where L-aspartic acid at position 5 is replaced by another proteinogenic amino acid, preferably L-valine, L-leucine and L-isoleucine, particularly preferably L-valine. EC No. 4.1.3.7 is assigned to citrate synthase.

L-Valine-producing coryneform bacteria typically have a feedback-resistant or desensitized acetolactate synthase (acetohydroxyacid synthase; EC No. 2.2.1.6). Feedback-resistant acetolactate synthase means an acetolactate synthase which, by comparison with the wild form, shows a lower sensitivity to inhibition by one or more of the amino acids selected from the group of L-valine, L-isoleucine and L-leucine, preferably L-valine.

The acetolactate synthase (IlvB, IlvN) of *Corynebacterium* consists of a so-called large subunit encoded by the ilvB gene and of a so-called small subunit encoded by the ilvN gene (Keilhauer et al., *J. Bacteriol.* 175(17)5595-5603 (1993)). WO 05/003357 and Elisakova et al. (*Appl. Environ. Microbiol.* 71(1):207-13 (2005)) report on variants of the IlvN subunit which confer resistance to L-valine, L-isoleucine and L-leucine on the acetolactate synthase. One variant comprises at position 21 of the amino acid sequence L-aspartic acid instead of L-isoleucine (IlvN I21D) and at position 22 L-phenylalanine instead of L-isoleucine (IlvN I22F). The second variant comprises at position 20 of the amino acid sequence L-aspartic acid instead of glycine (IlvN G20D), at position 21 of the amino acid sequence L-aspartic acid instead of L-isoleucine (IlvN I21D) and at position 22 L-phenylalanine instead of L-isoleucine (IlvN I22F). It is advantageous where appropriate to overexpress the genes which code for the wild form of acetolactate synthase, or the alleles which code for a feedback-resistant or desensitized acetolactate synthase.

The coryneform bacteria used for L-valine production may additionally have one or more of the features selected from the group:

a) overexpressed polynucleotide (ilvC gene) which codes for an isomeroreductase (IlvC, EC 1.1.1.86),
b) overexpressed polynucleotide (ilvD gene) which codes for a dihydroxy-acid dehydratase (IlvD, EC 4.2.1.9),
c) overexpressed polynucleotide (ilvE gene) which codes for a transaminase B (IlvE, EC 2.6.1.42), and
d) eliminated or attenuated activity of the E1p subunit encoded by the aceE gene of the pyruvate dehydrogenase complex (EC No. 1.2.4.1).

The ilvC gene of *C. glutamicum* coding for the isomeroreductase has been described for example by Keilhauer, et al. (*J. Bacteriol.* 175(17):5595-603 (1993) and in EP1108790 (see also access numbers C48648 and AX127147). The ilvD gene of *C. glutamicum* coding for the dihydroxy-dehydratase has been described for example in EP1006189 (see also access number AX136925). The ilvE gene of *C. glutamicum* coding for transaminase B (EC 2.6.1.42) is described for example in EP1108790 (see also access numbers AX127150 and AX122498). Joint overexpression of the ilvB, ilvN, ilvC and ilvD genes of *Corynebacterium glutamicum* can be achieved for example with the aid of the plasmid pECM3ilvBNCD described in EP 1 006 189. This plasmid is deposited in the form of the *Escherichia coli* K12 strain DH5αmcr/pECM3ilvBNCD as DSM12457 at the DSMZ. Measures for switching off and attenuating the aceE gene are described in EP 1 767 616.

The term "overexpression" describes in this connection an increase in the intracellular activity or concentration of one or more enzymes or proteins which are encoded by the corresponding DNA in a microorganism by, for example, increasing the copy number of the gene or genes or alleles or using a strong promoter. Numerous promoters which make it possible to adjust a desired concentration or activity of the polypeptide or of the enzyme are described in the prior art. For example, the lysC promoter of the mutant DM58-1, which is described in Kalinowski et al. (*Mol. Microbiol.* 5(5): 1197-1204 (1991), or the gap promoter, which is described in the patent application with the application number EP 06007373.1, can be employed. It is furthermore possible to employ the promoters described in the patent application with the application number EP 06117294.6, the promoters described by Patek, et al. (*J. Biotechnol.* 104(1-3):311-323 (2003), or the variants of the dapA promoter, for example the A25 promoter, described by Vasicova, et al. (*J. Bacteriol.* 181:6188-6191 (1999)).

It is also possible to employ promoters known from the genetics of *Escherichia coli*, such as, for example, tac promoter, trp promoter, trc promoter and lpp promoter or the $P_L$ and $P_R$ promoter of phage λ.

The gene or polynucleotide which has been provided with a promoter in such a way can be incorporated in the form of one (1) or more copies into the desired coryneform bacterium by using methods of transformation or conjugation as are sufficiently well known in the prior art, and where appropriate also by ballistic methods. It is possible to use for this purpose for example plasmids which are replicated by coryneform bacteria. A large number of such plasmids are described in the prior art. Suitable plasmid vectors are for example pZ1 (Menkel et al., *Appl. Environ. Microbiol.* 64:549-554 (1989) or the pSELF vectors described by Tauch et al. (*J. Biotechnol.* 99:79-91 (2002)). A review article on the topic of plasmids in *Corynebacterium glutamicum* is to be found in Tauch, et al. (*J. Biotechnol.* 104:27-40 (2003)).

A further possibility is to introduce one or more copies of the relevant gene, typically a maximum of 20, preferably a maximum of 10 to a maximum of 5, into the chromosome of a coryneform bacterium (gene amplification). In one embodiment, using for example methods described in Reinscheid et al. (*Appl. Environ. Microbiol.* 60:126-132 (1994)) for the hom-thrB operon, a plasmid which is non-replicative in *C. glutamicum* and which comprises the gene of interest is transferred into a coryneform bacterium. After homologous recombination by means of a crossover event, the resulting strain comprises at least two copies of the relevant gene.

In another embodiment, using for example methods described in WO 03/040373 and US-2003-0219881-A1, one or more copy (copies) of the gene of interest is introduced into a desired site in the chromosome of *C. glutamicum* by means of at least two recombination events.

In a further embodiment, using for example, methods described in WO 03/014330 and US-2004-0043458-A1, a tandem duplication of the gene can be achieved.

Finally, it is possible to adjust the copy number of the gene with the aid of transposons or IS elements (see: U.S. Pat. No. 5,804,414 or U.S. Pat. No. 5,591,577).

The concentration of overexpressed protein can be determined by 1- and 2-dimensional protein gel fractionation and subsequent visual identification of the protein concentration in the gel using appropriate evaluation software. A suitable method for preparing the protein gels in the case of coryneform bacteria and for identifying the proteins is the procedure described by Hermann, et al. (*Electrophoresis* 22:1712-23 (2001)). The protein concentration can likewise be determined by Western blot hybridization with an antibody specific for the protein to be detected (Sambrook, et al., Molecular cloning: a laboratory manual. 2nd Ed. Cold Spring Harbor Laboratory Press, Cold Spring Harbor, N.Y., 1989) and subsequent visual evaluation with appropriate software to determine the concentration (Lohaus, et al., *Biospektrum* 5:32-39 (1998); Lottspeich, Angewandte Chemie 38: 2630-2647 (1999)). It is likewise possible to use the enzyme assay described in the prior art to determine the activity.

Overexpression measures may increase the activity or concentration of the corresponding protein by at least 10%, 25%, 75%, 100%, 150%, 200%, 300%, 400% or 500%, maximally up to 1000% or 2000% based on that of the wild-type protein or of the activity or concentration of the protein in the starting microorganism.

In the work leading to the present invention it was found that coryneform bacteria in which the sugR gene is present in attenuated form, when cultured in a medium which comprises a carbon source which consists substantially of one or more of the sugars selected from the group of glucose, fructose and sucrose, and of one or more organic acids selected from the group of acetic acid, citric acid and pyruvic acid, preferably acetic acid, and/or alcohols, preferably glycerol, produce organic chemical compounds with an increased product formation rate compared with coryneform bacteria in which the sugR gene is present in the form of the wild-type gene or in which the sugR gene has not been attenuated.

The term "product formation rate" describes the increase in the product concentration per unit time. A useful unit is g/l·h (grams per liter and hour). The term specific product formation rate takes account of the concentration of the bacteria or of the biomass of bacteria at the given period or time. A useful unit is g(product)/g(biomass)·h (grams(product) per gram (biomass) and hour).

The invention accordingly also relates to a process for the fermentative preparation of organic chemical compounds, characterized in that it comprises the following steps:

a) culturing or fermentation of the recombinant coryneform bacteria which produce the desired organic chemical compound and in which the sugR gene is present in attenuated form, using a nutrient medium, and
b) under conditions with which the desired organic chemical compound is enriched or accumulated in the medium and/or in the cells, where the nutrient medium comprises a carbon source which substantially consists of one or more of the sugars selected from the group of glucose, fructose and sucrose, and one or more of the organic acids selected from the group of acetic acid, citric acid, pyruvic acid, preferably acetic acid, and/or alcohols, preferably glycerol, and where appropriate,
c) obtaining or isolating the desired organic chemical compound, with where appropriate further constituents of the fermentation broth and/or the biomass remain in their totality or in portions (>0 to 100%) in the final product, where the concentration of the organic chemical compound is measured where appropriate at one or more different times during the progress of the process. The bacteria which can be employed in step a) of the process include inter alia the coryneform bacteria described herein.

The produced microorganisms are cultured according to the invention in a batch process (batch cultivation), in a fed-batch process, in a repeated fed-batch process or in a continuous process. Summaries about such processes are available in the textbook by Chmiel (Bioprozesstechnik 1. Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

In a batch process, with few exceptions such as, for example, oxygen and pH-correcting means, all the starting materials are introduced in the form of a batch, and the microorganism is cultured in the resulting medium.

In a fed-batch process, the microorganism is initially cultured by means of a batch process (batch phase). Subsequently, a starting material which is essential for preparation of the product, where appropriate also a plurality of starting materials, is added continuously or discontinuously (feed phase). In the case of the preparation according to the invention of an organic chemical compound, this is a carbon source.

A repeated fed-batch process is a fed-batch process in which, after completion of the fermentation, part of the resulting fermentation broth is used as inoculum to start a renewed repeated fed-batch process. This cycle can be repeated where appropriate more than once. Repeated fed-batch processes are described for example in WO 02/18543 and WO 05/014843.

A continuous process entails a batch or fed-batch process being followed by continuous addition of one or more, where appropriate all, starting materials to the culture and, at the same time, removal of fermentation broth. Continuous processes are described for example in the patents U.S. Pat. No. 5,763,230, WO 05/014840, WO 05/014841 and WO 05/014842.

The culture medium or fermentation medium to be used must satisfy in a suitable manner the demands of the respective strains. The fermentation medium or the media employed during the fermentation comprise(s) all the substances or components ensuring growth of the microorganism and formation of the desired organic chemical compound. Descriptions of culture media of various microorganisms are to be found in the handbook "Manual of Methods for General Bacteriology" of the American Society of Bacteriology (Washington D.C., USA, 1981). The terms culture medium, fermentation medium and nutrient medium or medium are mutually exchangeable.

Descriptions of fermentation media are present inter alia in U.S. Pat. No. 6,221,636, in U.S. Pat. No. 5,840,551, in U.S. Pat. No. 5,770,409, in U.S. Pat. No. 5,605,818, in U.S. Pat. No. 5,275,940, in U.S. Pat. No. 4,275,157 and in U.S. Pat. No. 4,224,409. A culture medium generally comprises inter alia one or more carbon source(s), nitrogen source(s) and phosphorus source(s). The culture medium must additionally comprise salts of metals such as, for example, magnesium sulfate or iron sulfate, which are necessary for growth. Finally, essential growth factors such as amino acids and vitamins may be employed in addition to the abovementioned substances.

Carbon source means in the context of this invention compounds which comprise only carbon, oxygen and hydrogen in the molecule and are utilized by the microorganisms to form their biomass and to produce an organic chemical compound. The carbon source in the process of the invention consists essentially of one or more of the sugars selected from the group of glucose, fructose and sucrose, and one or more of the organic acids selected from the group of acetic acid, citric acid and pyruvic acid. In the case of organic acids, acetic acid is preferred. Mixtures of sugars and organic acids may result inter alia on hydrolysis of lignocellulose.

A preferred process is one in which the carbon source consists essentially of a mixture of one or more of the sugars selected from the group of glucose, fructose and sucrose, and acetic acid. Preference is given to glucose, sucrose and sugar mixtures essentially consisting of glucose and fructose, or sugar mixtures essentially consisting of sucrose, glucose and fructose. Very particular preference is given to glucose- and sucrose-containing mixtures.

The term "essentially" takes account of the fact that not only chemically pure starting materials but also, where appropriate, impure starting materials of technical or lower quality are used in industrial fermentation processes to prepare organic chemical compounds. The term further takes account of the composition of typical complex microbiological media constituents, the chemical change in the starting materials as a result of sterilization by heat, and finally the transfer, resulting through the inoculation of a nutrient medium by means of a preculture (an inoculum), of media constituents or constituents of the fermentation broth.

The term "acetic acid" includes not only the acid itself but also the salts of acetic acid such as the ammonium salt, the alkali metal salts, for example the potassium salt, or the alkaline earth metal salts, for example the calcium salt. It is possible to use in a process of the invention not only chemically pure acetic acid but also acetic acid of technical quality. Acetic acid of technical quality comprises low concentrations of compounds which arise in the preparation process and have not been completely removed.

Starch hydrolyzates are an important source of glucose. Accordingly, concomitant substances are typically for example maltose and/or isomaltose in concentrations of approximately 0.1 to 2% by weight. The glucose used for the measures of the invention has a content of ≥(at least) 90% by weight, preferably ≥95% by weight (based on dry matter).

It is known that the sucrose in sucrose solutions is converted to glucose and fructose to a small extent at elevated temperature like that present for example during heat sterilization. The content of glucose and fructose in the sucrose or sucrose solution employed for the measures of the invention is ≤(not more than) 10% by weight, preferably ≤5% by weight (based on dry matter). The molasses resulting from the production of sucrose from sugarbeet (beet molasses) comprises a sugar mixture which consists essentially of sucrose.

Concentrated solutions comprising glucose and fructose are known to skilled persons for example under the designation "isosyrup", "high fructose corn syrup" or "fructose-containing glucose syrup". These are prepared by hydrolysis of starch with subsequent treatment of the glucose with isomerase. They comprise a sugar mixture which generally comprises approximately 50-55% by weight glucose and 40-45% by weight fructose (based on dry matter). Owing to the preparation process, such syrups generally comprise inter alia maltose in a concentration not exceeding approximately 6% by weight (based on dry matter).

Concentrated solutions essentially comprising a sugar mixture consisting of equimolar portions of glucose and fructose are likewise known to skilled persons. These solutions are prepared for example by treating sucrose with invertase and therefore generally comprise small amounts of sucrose (≤5% by weight based on dry matter). Concentrated solutions comprising a sugar mixture consisting of sucrose, glucose and fructose are further known to skilled persons. These solutions are prepared by partial inversion of sucrose. One known concentrate consists of 38.5% by weight sucrose, 38.5% by weight invert sugar (i.e., glucose and fructose in the ratio 1:1) and 23% by weight water. The molasses resulting from the production of sucrose from sugar cane (sugar cane molasses) comprises a sugar mixture which consists essentially of sucrose, glucose and fructose.

The sugar mixtures described above are suitable as carbon source for the process of the invention.

The term "essentially" further takes account of the fact that complex media constituents employed in the fermentation medium, such as, for example, yeast extract or corn steep liquor, comprise varying proportions of compounds able to serve as carbon source. Thus, yeast extract comprises inter alia trehalose and/or glucose. Corn steep liquor comprises approximately 10 to 20% by weight (based on dry matter) lactic acid. Such complex media constituents are generally employed if necessary in a concentration of 0.5 to 20 g/l and also in higher concentrations in the fermentation medium.

Information on the production of glucose, sucrose and fructose and on the composition of complex media constituents are to be found inter alia in the textbooks by Bartens (Zuckertechnologie, Rüben and Rohrzuckerherstellung, Verlag Dr. Albert Bartens K G, Berlin (Germany)), McGinnis (Beet-Sugar Technology, third edition, Studio of Printcraft, Fort Collins, Colo., US (1982)), Drews (Mikrogiologisches Praktikum, 3rd edition, Springer Verlag, Berlin (Germany), 1976), Rehm (Industrielle Mikrobiologie, 2nd edition, Springer Verlag, Berlin (Germany), 1980) and Crueger and Crueger (Lehrbuch der Angewandten Mikrobiologie, Akademische Verlagsgesellschaft, Wiesbaden (Germany), 1982).

The term "essentially" finally takes account the fact that inoculation of a nutrient medium by using a so-called preculture (inoculum) transfers carbon sources which have not been consumed or have been formed during the preculture into the culture used to prepare the respective organic chemical compound. The proportion of the preculture in the culture resulting from the inoculation generally amounts to from 2 to 20%, where appropriate also not more than 50%.

The acetic acid employed in a process of the invention generally consists of ≥(at least) 90% by weight, preferably at least 92.5% by weight and particularly preferably ≥95% by weight of acetic acid (based on the anhydrous starting material). Acetic acid with a purity of ≥97% by weight, ≥98% by weight or ≥99% by weight can likewise be employed.

The sugar preferably employed, or the sugar mixtures preferably employed, in a process of the invention generally consist(s) of ≥(at least) 90% by weight, where appropriate preferably ≥95% by weight, of one or more of the stated sugars selected from the group of glucose, sucrose and fructose (based on dry matter).

If mixtures consisting of acetic acid and glucose, or mixtures consisting of acetic acid and sucrose, are employed in a process of the invention, the proportion of acetic acid in the mixture is ≥(at least) 5% by weight, ≥10% by weight, ≥20% by weight, ≥40% by weight, ≥50% by weight, ≥60% by weight, or ≥80% by weight and ≤(at most)≤90% by weight or ≤(at most) 95% by weight.

If mixtures consisting of acetic acid and of a sugar mixture composed of glucose and fructose are employed in a process of the invention, the proportion of acetic acid in the mixture is ≥(at least) 5% by weight, ≥10% by weight, ≥20% by weight, ≥40% by weight, ≥50% by weight, ≥60% by weight, or ≥80% by weight and ≤(at most) 90% by weight. The proportion of glucose in the sugar mixture consisting of glucose and fructose is ≥(at least) 5% by weight, ≥10% by weight, ≥20% by weight, ≥40% by weight, ≥50% by weight, ≥60% by weight, or ≥80% by weight and ≤(at most) 90% by weight, preferably 45 to 65% by weight, 50 to 60% by weight, 50 to 60% by weight, 55 to 65% by weight or 55 to 60% by weight.

If mixtures consisting of acetic acid and of a sugar mixture composed of sucrose, glucose and fructose are employed in a process of the invention, the proportion of acetic acid in the mixture is ≥(at least) 5% by weight, ≥10% by weight, ≥20% by weight, ≥40% by weight, ≥50% by weight, ≥60% by weight, or ≥80% by weight and ≤(at most) 90% by weight or ≤(at most) 95% by weight. The proportion of sucrose, glucose and fructose in the sugar mixture is in each case >(more than) 10% by weight and less than 80% by weight.

The total amount of the individual components in the mixture of the carbon sources adds up to 100% by weight. The carbon sources are naturally present in the fermentation media in the form of aqueous solutions.

The concentration of acetic acid during the fermentation generally does not exceed 40 g/l or 30 g/l. The concentration of acetic acid during the fermentation is where appropriate not more than 20 g/l, 10 g/l, 5 g/l or 2.5 g/l. If acetic acid and one or more of the sugars selected from the group of glucose, sucrose and fructose is employed as carbon source in a process of the invention, the medium or the fermentation broth in the case of the batch process accordingly then comprises at least at the start of the process acetic acid and the stated sugar(s) as carbon source.

In the case of a fed-batch process, the carbon source, i.e. said sugars and the acetic acid, can be introduced into the process in various ways. In a first aspect, one or more of the stated sugars is introduced for the batch phase. In the subsequent feed phase,
  a) acetic acid, or
  b) a mixture of acetic acid and one or more of the stated sugars is employed. The feed phase preferably starts before the sugar(s) introduced at the start of the batch phase has (have) been completely consumed.

In a second aspect, acetic acid is introduced for the batch phase. In the subsequent feed phase,
  a) a mixture of acetic acid and one or more of the stated sugars is employed, or
  b) a mixture of one or more of the stated sugars is employed.

The feed phase preferably starts before the acetic acid introduced at the start of the batch phase has been completely consumed.

In a third aspect, a mixture of acetic acid and one or more of the stated sugars is introduced for the batch phase. In the subsequent feed phase,
  a) acetic acid, or
  b) a mixture of acetic acid and one or more of the stated sugars is employed.

In a fourth aspect, a carbon source selected from the group of: a) acetic acid; b) one or more of the stated sugars; and c) a mixture of acetic acid and one or more of the sugars selected from the group of sucrose, glucose and fructose; is introduced for the batch phase. In the subsequent feed phase: d) acetic acid is employed in at least one continuous period of at least one (1) hour and not more than 100, preferably not more than 50, particularly preferably not more than 30 hours, and subsequently one or more of the stated sugars is employed in at least one continuous period of at least one (1) hour and not more than 100, preferably not more than 50, particularly preferably not more than 30 hours; or e) one or more of the stated sugars is employed in at least one continuous period of at least one (1) hour and not more than 100, preferably not more than 50, particularly preferably not more than 30 hours, and subsequently acetic acid is employed in at least one continuous period of at least one (1) hour and not more than 100, preferably not more than 50, particularly preferably not more than 30 hours, where the proportion of acetic acid in the carbon source employed is ≥(at least) 5% by weight, ≥10% by weight, ≥20% by weight, ≥40% by weight, ≥50% by weight, ≥60% by weight, or ≥80% by weight and ≤(at most) 90% by weight or ≤(at most) 95% by weight. The feed phase preferably starts before the carbon source(s) introduced at the start of the batch phase has (have) been completely consumed. The term "completely consumed" means that the respective carbon source is no longer detectable in the fermentation broth.

In the fed-batch processes, the third aspect mentioned with case b) is preferred.

In the case of a repeated fed-batch process, the carbon sources employed for repeated batch and feed phases are as described for the batch process and fed-batch process (see above).

In the case of a continuous culture, acetic acid and one or more of the sugars selected from the group of sucrose, glucose and fructose are added continuously.

It is possible to employ as a nitrogen source inorganic compounds such as ammonium sulfate, ammonium chloride, ammonium phosphate, ammonium carbonate and ammonium nitrate, preferably ammonium sulfate, and organic compounds such as urea. The nitrogen sources can be used singly or as mixture. Additionally employed where appropriate are organic nitrogen-containing substance mixtures such as peptones, yeast extract, meat extract, corn steep liquor or soya flour.

It is possible to use as phosphorus source phosphoric acid, potassium dihydrogenphosphate, dipotassium hydrogenphosphate or the corresponding sodium-containing salts, singly or as mixture.

Fermentations is generally carried out at a pH of from 5.5 to 9.0, in particular 6.0 to 8.0. To control the pH of the culture, basic compounds such as sodium hydroxide, potassium hydroxide, ammonia or aqueous ammonia or acidic compounds such as phosphoric acid or sulfuric acid are employed in a suitable manner. To control foaming it is possible to employ antifoams such as, for example, fatty acid polyglycol esters. To maintain the stability of plasmids it is possible to add suitable selectively acting substances, for example antibiotics, to the medium. In order to maintain aerobic conditions, oxygen or oxygen-containing gas mixtures such as, for example, air are introduced into the culture.

The temperature of the culture is normally 25° C. to 45° C. and preferably 30° C. to 40° C. The activity of the microorganisms results in an enrichment or accumulation of the organic chemical compound in the fermentation or culture broth. The culture is continued until formation of the desired organic chemical compound is maximal. This aim is normally achieved within 10 hours to 160 hours. Longer culturing times are possible in continuous processes.

A "fermentation broth" or "culture broth" refers to a fermentation medium in which a microorganism has been cultured for a certain time and at a certain temperature. When the fermentation is complete, the resulting fermentation broth accordingly comprises a) the biomass produced as a result of the growth of the cells of the microorganism, b) the organic chemical compound formed during the fermentation, c) the organic by-products formed during the fermentation, and d) the constituents of the fermentation medium/media employed or of the starting materials such as, for example, vitamins such as thiamine or salts such as magnesium sulfate, which have not been consumed by the fermentation.

The produced culture or fermentation broth is then collected and the desired organic chemical compound present in the fermentation broth, and the product comprising the desired organic chemical compound are obtained or isolated. A solid or liquid product is then obtained by further processing steps. In this way, the desired organic chemical compound present in the fermentation broth is converted into a desired product formed.

Methods for determining organic chemical compounds are known in the prior art. Analysis of, for example, L-amino acids can take place as described by Spackman, et al. (*Anal. Chem.* 30:1190 (1958)) by anion exchange chromatography with subsequent ninhydrin derivatization, or it can take place by reversed phase HPLC as described by Lindroth, et al. (*Anal. Chem.* 51:1167-1174 (1979)).

In the case of the amino acid L-lysine, substantially four different product forms are known in the state of the art. One group of L-lysine-containing products includes concentrated aqueous alkaline solutions of purified L-lysine (EP-B-0534865). A further group as described for example in U.S. Pat. No. 6,340,486 and U.S. Pat. No. 6,465,025 includes aqueous acidic biomass-containing concentrates of L-lysine-containing fermentation broths. The best-known group of solid products includes powder or crystalline forms of purified or pure L-lysine which is typically in the form of a salt such as, for example, L-lysine monohydrochloride. A further group of solid product forms is described for example in EP-B-0533039. Besides L-lysine, the product form described therein comprises most of the starting materials which were used during the fermentative production and were not consumed and, where appropriate, the biomass of the microorganism employed with a content of >0%-100%.

In the case of the amino acids L-valine, L-isoleucine, L-proline, L-tryptophan and L-homoserine, the product forms known in the prior art are substantially those containing the relevant amino acids in purified or pure form (>95% by weight or >98% by weight).

Corresponding to the different product forms, a wide variety of processes are known with which the L-amino acid is collected, isolated or purified from the fermentation broth in order to produce the L-amino acid-containing product or the purified L-amino acid.

Solid pure L-amino acids are produced substantially by using methods of ion exchange chromatography, where appropriate with use of activated carbon, and methods of crystallization. In the case of lysine, the corresponding base or a corresponding salt such as, for example, the monohydrochloride (Lys-HCl) or lysine sulfate (Lys$_2$-H$_2$SO$_4$) is obtained in this way.

In the case of lysine, EP-B-0534865 describes a process for producing aqueous, basic L-lysine-containing solutions from fermentation broths. In the process described therein, the biomass is removed from the fermentation broth and discarded. A base such as, for example, sodium, potassium or ammonium hydroxide is used to adjust a pH of between 9 to 11. The mineral constituents (inorganic salts) are removed from the broth after concentration and cooling by crystallization and either used as fertilizers or discarded.

In processes for producing lysine using the bacteria according to the invention, processes resulting in products which comprise components of the fermentation broth are also employed. These are used in particular as animal feed additives.

Biomass can be removed wholly or partly from the fermentation broth by separation methods such as, for example, centrifugation, filtration, decantation or a combination thereof, or be left completely therein. Where appropriate, the biomass or the biomass-containing fermentation broth is inactivated during a suitable process step, for example by thermal treatment (heating) or by addition of acid. The chemical constituents of the biomass are, inter alia, the cell envelope, for example the peptidoglycan and the arabinogalactan, the protein or polypeptide, lipids and phospholipids and nucleic acids (DNA and RNA).

In one procedure, the biomass is removed completely or almost completely so that no (0%) or not more than 30%, not more than 20%, not more than 10%, not more than 5%, not more than 1% or not more than 0.1% biomass remains in the product produced. In a further procedure, the biomass is not removed, or is removed only in small proportions, so that all (100%) or more than 70%, 80%, 90%, 95%, 99% or 99.9% biomass remains in the product produced. In one process according to the invention, accordingly, the biomass is removed in proportions ≥ to 0% to ≤100%.

Finally, the fermentation broth obtained after the fermentation can be adjusted, before or after the complete or partial removal of the biomass, to an acidic pH with an inorganic acid such as, for example, hydrochloric acid, sulfuric acid or phosphoric acid or organic acid such as, for example, propionic acid (GB 1,439,728 or EP 1 331 220). It is likewise possible to acidify the fermentation broth with the complete content of biomass (U.S. Pat. No. 6,340,486 or U.S. Pat. No. 6,465,025). Finally, the broth can also be stabilized by adding sodium bisulfite (NaHSO$_3$, GB 1,439,728) or another salt, for example ammonium, alkali metal or alkaline earth metal salt of sulfurous acid.

During the removal of the biomass, organic or inorganic solids present where appropriate in the fermentation broth are partially or completely removed. The organic by-products dissolved in the fermentation broth and the dissolved unconsumed components of the fermentation medium (starting materials) remain at least partly (>0%), preferably to the extent of at least 25%, particularly preferably to the extent of at least 50% and very particularly preferably to the extent of at least 75% in the product. Where appropriate, they also remain completely (100%) or almost completely, meaning >95% or >98%, in the product. In this sense, the term "based on fermentation broth" means that the product comprises at least part of the components of the fermentation broth. in addition of the desired organic chemical compound.

Subsequently, water is removed from the broth by known methods such as, for example, with the aid of a rotary evaporator, thin-film evaporator, falling film evaporator, by reverse osmosis or by nanofiltration. This concentrated fermentation broth can then be worked up to free-flowing products, in particular to a fine-particle powder or preferably coarse granules, by methods of freeze drying, of spray drying, of spray granulation or by other processes as described for example in the circulating fluidized bed according to PCT/EP2004/006655. A desired product is isolated where appropriate from the resulting granules by screening or dust removal. It is likewise possible to dry the fermentation broth directly, i.e. without previous concentration by spray drying or spray granulation.

"Free-flowing" means powders which flow unimpeded out of a series of glass orifice vessels with orifices of different sizes at least out of the vessel with a 5 mm (millimeters) orifice (Klein: Seifen, Öle, Fette, Wachse 94, 12 (1968)).

"Fine-particle" means a powder predominantly (>50%) of a particle size of diameter from 20 to 200 μm.

"Coarse" means a product predominantly (>50%) of a particle size of diameter from 200 to 2000 μm.

The particle size determination can be carried out by methods of laser diffraction spectrometry. Corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, published by Wiley & Sons (1998).

The free-flowing, fine-particle powder can in turn be converted by suitable compaction or granulation processes into a coarse, very free-flowing, storable and substantially dust-free product.

The term "dust-free" means that the product comprises only small proportions (<5%) of particle sizes below 100 μm in diameter.

"Storable" in the sense of this invention means a product which can be stored for at least one (1) year or longer, preferably at least 1.5 years or longer, particularly preferably two (2) years or longer, in a dry and cool environment without any substantial loss (<5%) of the respective amino acid occurring.

The invention accordingly further relates to a process for producing an L-amino acid, preferably L-lysine or L-tryptophan, containing product, preferably animal feed additive, from fermentation broths, characterized by the steps
a) culturing and fermentation of an L-amino acid-secreting coryneform bacterium in which the sugR gene is present in attenuated form, in a fermentation medium, and accumulation of the L-amino acid,
b) removal of the biomass formed during the fermentation in an amount of from 0 to 100% by weight, and
c) drying of the fermentation broth obtained as in a) and/or b) in order to obtain the product in the desired powder or granular form,
where an acid selected from the group of sulfuric acid, phosphoric acid or hydrochloric acid is added where appropriate before step b) or c). Step a) or b) is preferably followed by removal of water from the L-amino acid-containing fermentation broth (concentration). In addition, the concentration of the L-amino acid is measured where appropriate at one or more of the process stages.

The invention further relates to a process for producing a lysine sulfate-containing product which is described in principle in DE 102006016158, and in which the fermentation broth obtained using the microorganisms according to the invention, from which the biomass has been removed completely or partly where appropriate, is further processed by carrying out a process which includes at least the following steps:

a) the pH is reduced by adding sulfuric acid to 4.0 to 5.2, in particular 4.9 to 5.1, and a molar sulfate/L-lysine ratio of from 0.85 to 1.2, preferably 0.9 to 1.0, particularly preferably >0.9 to <0.95, is adjusted in the broth, where appropriate by adding a further or a plurality of sulfate-containing compound(s) and b) the mixture obtained in this way is concentrated by removal of water, and granulated where appropriate, where one or both of the following measures is/are carried out where appropriate before step a):

c) measurement of the molar sulfate/L-lysine ratio to ascertain the required amount of sulfate-containing compound(s)

d) addition of a sulfate-containing compound selected from the group of ammonium sulfate, ammonium bisulfate and sulfuric acid in appropriate ratios.

Where appropriate, also before step b), a salt of sulfurous acid, preferably alkali metal bisulfite, particularly preferably sodium bisulfite, is added in a concentration of 0.01 to 0.5 by weight, preferably 0.1 to 0.3% by weight, particularly preferably 0.1 to 0.2% by weight, based on the fermentation broth.

Preferred sulfate-containing compounds which should be mentioned in the context of the abovementioned process steps are in particular ammonium sulfate and/or ammonium bisulfate or corresponding mixtures of ammonia and sulfuric acid and sulfuric acid itself.

The molar sulfate/L-lysine ratio V is calculated by the formula: $V=2\times[SO_4^{2-}]/[L\text{-lysine}]$. This formula takes account of the fact that the $SO_4^{2-}$ anion has two charges. A ratio of V=1 means that the stoichiometric composition $Lys_2(SO_4)$ is present, whereas the finding with a ratio of V=0.9 is a 10% sulfate deficit and with a ratio of V=1.1 is a 10% sulfate excess.

It is advantageous to employ during the granulation or compaction the usual organic or inorganic auxiliaries or carriers such as starch, gelatin, cellulose derivatives or similar substances, as normally used in the processing of food products or feeds as binders, gelling agents or thickeners, or further substances such as, for example, silicas, silicates (EP0743016A) or stearates.

It is further advantageous to provide the surface of the resulting granules with oils as described in WO 04/054381. Oils which can be used are mineral oils, vegetable oils or mixtures of vegetable oils. Examples of such oils are soya oil, olive oil, soya oil/lecithin mixtures. In the same way, silicone oils, polyethylene glycols or hydroxyethylcellulose are also suitable. Treatment of the surfaces with the said oils achieves an increased abrasion resistance of the product and a reduction in the dust content. The oil content in the product is 0.02 to 2.0% by weight, preferably 0.02 to 1.0% by weight, and very particularly preferably 0.2 to 1.0% by weight based on the total amount of the feed additive.

Preferred products have a proportion of ≥97% by weight of a particle size of from 100 to 1800 μm or a proportion of ≥95% by weight of a particle size of from 300 to 1800 μm diameter. The proportion of dust, i.e. particles with a particle size <100 μm, is preferably >0 to 1% by weight, particularly preferably not exceeding 0.5% by weight.

However, alternatively, the product may also be adsorbed on an organic or inorganic carrier known and customary in the processing of feeds, such as, for example, silicas, silicates, meals, brans, flours, starches, sugars or others, and/or be mixed and stabilized with customary thickeners and binders. Examples of use and processes therefor are described in the literature (Die Mühle+Mischfuttertechnik 132 (1995) 49, page 817).

Finally, the product can also be brought by coating processes with film-formers such as, for example, metal carbonates, silicas, silicates, alginates, stearates, starches, gums and cellulose ethers as described in DE-C-4100920 to a state in which it is stable to digestion by animal stomachs, especially the stomach of ruminants.

To adjust a desired amino acid concentration in the product it is possible, depending on requirements, to add the appropriate amino acid during the process in the form of a concentrate or, if appropriate, of a substantially pure substance or its salt in liquid or solid form. These can be added singly or as mixtures to the resulting or concentrated fermentation broth, or else during the drying or granulation process.

The invention further relates to a process for producing a solid lysine-containing product as described in principle in US 20050220933, and which includes the working up of the fermentation broth obtained using the microorganisms according to the invention, in the following steps:

a) filtration of the fermentation broth, preferably with a membrane filter, to result in a biomass-containing sludge and a filtrate, b) concentration of the filtrate, preferably so as to result in a solids content of from 48 to 52% by weight, c) granulation of the concentrate obtained in step b), preferably at a temperature of from 50° C. to 62° C., and d) coating of the granules obtained in c) with one or more of the coating agent(s).

The coating agents used for the coating in step d) are preferably selected from the group consisting of d1) the biomass obtained in step a), d2) an L-lysine-containing compound, preferably selected from the group of L-lysine hydrochloride or L-lysine sulfate, d3) a substantially L-lysine-free substance with an L-lysine content of <1% by weight, preferably <0.5% by weight, preferably selected from the group of starch, carageenan, agar, silicas, silicates, meals, brans and flours, and d4) a water-repellent substance, preferably selected from the group of oils, polyethylene glycols and liquid paraffins.

In the case of lysine, the ratio of the ions during the production of lysine-containing products is preferably adjusted so that the equivalent ion ratio corresponding to the following formula $2\times[SO_4^{2-}]+[Cl^-]-[NH_4^+]-[Na^+]-[K^+]-2\times[Mg^{2+}]-2\times[Ca^{2+}]/[L\text{-Lys}]$ results in 0.68 to 0.95, preferably 0.68 to 0.90, as described by Kushiki et al. in US 20030152633 (the molar concentrations are to be given in the "[ ]").

In the case of lysine, the solid product produced in this way has, based on the fermentation broth, a lysine content (as lysine base) of 10% by weight to 70% by weight or 20% by weight to 70% by weight, preferably 30% by weight to 70% by weight and very particularly preferably of 40% by weight to 70% by weight, based on the dry matter of the product. Maximum contents of lysine base of 71% by weight, 72% by weight, 73% by weight are likewise possible.

The water content of the solid product is up to 5% by weight, preferably up to 4% by weight, and particularly preferably less than 3% by weight.

The invention therefore relates to an L-lysine-containing feed additive based on fermentation broth, which exhibits the following features a) a lysine content (as base) of at least 10% by weight up to a maximum of 73% by weight, b) a water content not exceeding 5% by weight, and c) a biomass content corresponding to at least 0.1% of the biomass present in the fermentation broth, where the biomass, inactivated where appropriate, is formed by coryneform bacteria according to the invention.

The present invention is explained in more detail below on the basis of exemplary embodiments.

EXAMPLES

Example 1

Deletion of the sugR Gene

Chromosomal DNA was isolated from the strain ATCC 13032 by the method of Eikmanns et al. (*Microbiol.* 140: 1817-1828 (1994)). On the basis of the known *C. glutamicum* sugR gene sequence from the database of the National Center for Biotechnology Information (NCBI) of the National Library of Medicine (Bethesda, Md., USA), under Accession Number NC_003450 (Region: 2037815-2038594, synonym NCgl1856) and Accession Number NC_006958 (Region: 2007864-2008643, synonym cg2115), the oligonucleotides described below were selected for generation of the sugR deletion allele by means of the polymerase chain reaction (PCR) according to the "Splicing by Overlap Extension" method (Gene SOEing method) (Horton, Molecular Biotechnology 3: 93-98 (1995)):

```
Primer sugR_A (SEQ ID NO: 14):
5'- GC GAATTC ACA AGG ATT CAT

CTG GCA TC -3'

Primer sugR_B (SEQ ID NO: 15):
5'- CCCATCCACTAAACTTAAACA GCG

CTC CTC TGC GTA CAT -3'

Primer sugR_C (SEQ ID NO: 16):
5'- TGTTTAAGTTTAGTGGATGGG CGA

GAA CGC GAT GTA GAA GTT GTG -3'

Primer sugR_D (SEQ ID NO: 17):
5'- GC GGATCC CAA ATT GCC ACC

CAA CAA CAC CC -3'
```

The primers shown were synthesized by MWG Biotech (Ebersberg, Germany) and the PCR reaction was carried out using Pfu polymerase (Stratagene, Product NO: 600135, La Jolla, USA).

The primers sugR_B and sugR_C are composed of two regions, a sequence of nucleotides which binds to the nucleotides 1 to 18 and 745 to 768, respectively, within the coding sequence of sugR (see SEQ ID NO:1), and a linker of 21 bp in length. The sequences of the sugR_A and sugR_D primers are modified so as to produce recognition sites for restriction enzymes. The EcoRI recognition sequence is chosen for the sugR_A primer and the BamHI recognition sequence is chosen for the sugR_D primer, both of which are indicated by underlining in the sequence of nucleotides depicted above.

With the aid of the polymerase chain reaction, the sugR_A and sugR_B primers enable a 464 bp DNA fragment to be amplified and the sugR_C and sugR_D primers enable a 472 bp DNA fragment to be amplified. The amplicons are verified by electrophoresis in a 0.8% strength agarose gel, isolated from said agarose gel using the High Pure PCR Product Purification Kit (Product NO: 1732676, Roche Diagnostics GmbH, Mannheim, Germany) and used together as template for another PCR reaction using the sugR_A and sugR_D primers. In this way the 915 bp sugR deletion derivative is generated (see also SEQ ID NO: 18).

The product amplified in this way is verified by electrophoresis in a 0.8% strength agarose gel.

Example 2

Cloning of the sugR Deletion Derivative into the pGEM-T Vector

The 915 bp amplified DNA fragment carrying the sugR deletion derivative was ligated by T4 DNA ligase (pGem-T Vector System, Promega, Wis., USA) into the pGEM-T vector (Promega, Wis., USA).

Subsequently, the *E. coli* strain DH5α (Grant, et al., *Proc. Nat'l Acad. Sci. USA* 87:4645-4649 (1990)) is transformed with the ligation mixture according to Hanahan (Techniques for transformation of *E. coli*, p. 109-135 (1985). In G.D.M. (ed.), DNA cloning, vol. 1, IRL-Press, Oxford/Washington D.C.). Plasmid-carrying cells are selected by plating out the transformation mixture on LB agar (Sambrook et al., Molecular Cloning: A Laboratory Manual. 2nd Ed., Cold Spring Harbor Laboratory Press, Cold Spring Harbor, N.Y., 1989) supplemented with 25 mg/l kanamycin. Plasmid DNA is isolated from a transformant with the aid of the QIAprep Spin Miniprep Kit from Qiagen (Hilden, Germany) and checked by treatment with the restriction enzymes BamHI and EcoRI or BglI and subsequent agarose gel electrophoresis (0.8%). The plasmid is referred to as pGEM-T_delsugR. The sugR deletion derivative was verified by sequencing (Agowa GmbH, Berlin, Germany). The sequence is depicted in SEQ ID NO: 18.

Example 3

Construction of the Exchange Vector pK19mobsacB_deltasugR

The sugR deletion derivative is isolated from the plasmid described in Example 2, pGEM-T_delsugR, by complete cleavage with the enzymes EcoRI and BamHI. After fractionation in an agarose gel (0.8%), the approx. 0.9 kb fragment carrying the sugR deletion derivative is isolated from said agarose gel using the High Pure PCR Product Purification Kit (Product NO: 1732676, Roche Diagnostics GmbH, Mannheim, Germany).

The sugR deletion derivative obtained in this way is used for ligation with the mobilizable cloning vector pK19mobsacB (Schäfer, et al., *Gene* 14:69-73 (1994)). The latter has been cleaved completely beforehand, using the restriction endonucleases EcoRI and BamHI. The vector prepared in this way is mixed with the sugR deletion allele and treated with T4 DNA ligase (Amersham Pharmacia, Freiburg, Germany).

The *E. coli* strain DH5α (Grant, *Proc. Nat'l Acad. Sci. USA* 87:4645-4649 (1990)) is then electroporated with the ligation mixture (Hanahan, In. DNA Cloning. A Practical Approach, Vol. 1, ILR-Press, Cold Spring Harbor, N.Y., 1989). The plasmid-carrying cells are selected by plating out the transformation mixture on LB agar (Sambrook et al., Molecular Cloning: A Laboratory Manual. 2nd Ed., Cold Spring Harbor, N.Y., 1989) supplemented with 25 mg/l kanamycin.

Plasmid DNA is isolated from a transformant with the aid of the QIAprep Spin Miniprep Kit from Qiagen, and the cloned sugR deletion allele is verified by means of restriction cleavage with the restriction endonucleases EcoRI and BamHI or PvuII. The plasmid is referred to as pK19mobsacB_deltasugR and is depicted in FIG. 1. The strain is referred to as *E. coli*H5α/pK19mobsacB_deltasugR.

Example 4

Deletion Mutagenesis of the SugR Gene in *C. glutamicum* DM1729

The *Corynebacterium glutamicum* strain DM1729 is a mutant of *Corynebacterium glutamicum* ATCC13032, which carries the alleles pyc P458S, hom V59A and lysC T311I and has been deposited under the name DSM17576 with the Deutsche Sammlung für Mikroorganismen and Zellkulturen [German Collection of Microorganisms and Cell Cultures] (DSMZ, Braunschweig, Germany) on Sep. 16, 2005.

The vector specified in Example 3, pK19mobsacB_deltasugR, was electrophorated by the electrophoration method of van der Rest, et al. (*Appl. Microbiol. Biotechnol.* 52:541-545 (1999)) into the *Corynebacterium glutamicum* strain DM1729 (conditions: 25 μF, 600 S2 and 2.5 kV/cm (Bio-Rad Gene Pulser Xcell, Bio-Rad Laboratories, Hercules, Canada)).

The vector cannot self-replicate in DM1729 and is retained in the cell only if it has integrated into the chromosome as a result of a recombination event. Clones with integrated pK19mobsacB_deltasugR are selected by plating out the conjugation mixture on LB agar (Sambrook et al., Molecular Cloning: A Laboratory Manual, 2nd Ed., Cold Spring Harbor, N.Y., 1989) supplemented with 15 mg/l kanamycin and 50 mg/ml nalidixic acid. Established clones are streaked out on LB agar plates containing 25 mg/l kanamycin and incubated at 33° C. for 16 hours. Mutants in which the plasmid has been excized as a result of a second recombination event are selected by culturing the clones unselectively in liquid LB medium for 20 hours, then streaking them out on LB agar containing 10% sucrose and incubating them for 24 hours.

Like the starting plasmid, pK19mobsacB, the pK19mobsacB_deltasugR plasmid contains, in addition to the kanamycin resistance gene, a copy of the sacB gene coding for the *Bacillus subtilis* levan sucrase. Sucrose-inducible expression produces levan sucrase which catalyses the synthesis of the product levan which is toxic to *C. glutamicum*. As a result, only those clones grow on LB agar containing sucrose, in which the integrated pK19mobsacB_deltasugR has been excized again. Excision may comprise excision of either the complete chromosomal copy of the sugR gene or of the incomplete copy containing the internal deletion, together with the plasmid.

Approximately 40 to 50 colonies are tested for the phenotype "growth in the presence of sucrose" and "non-growth in the presence of kanamycin". In order to prove that the deleted sugR allele has remained in the chromosome, 8 colonies having the phenotype "growth in the presence of sucrose" and "non-growth in the presence of kanamycin" are studied by the standard PCR method of Innis et al. (PCR Protocols. A Guide to Methods and Applications, 1990, Academic Press) with the aid of the polymerase chain reaction. In the process, a DNA fragment is amplified from the chromosomal DNA of the colonies, which carries the sugR gene and surrounding regions. The following primer oligonucleotides are selected for PCR.

```
sugR-k-for (SEQ ID NO: 19):
5' GTT CGT CGC GGC AAT GAT TGA CG 3'
```

```
sugR-k-rev (SEQ ID NO: 20):
5' CTC ACC ACA TCC ACA AAC CAC GC 3'
```

In the case of control clones with complete sugR allele, the primers enable an approx. 1.7 kb DNA fragment to be amplified. In the case of clones having a deleted sugR allele, DNA fragments of approx. 0.96 kb are amplified.

The amplified DNA fragments are identified by means of electrophoresis in a 0.8% strength agarose gel. In this way, 6 of the strain DM1729 clones assayed were shown to carry a deleted sugR allele on their chromosome. One of the clones was referred to as *C. glutamicum* DM1729deltasugR.

Example 5

Preparation of Lysine

The *C. glutamicum* strain obtained in Example 4, DM1729deltasugR, is cultured in a nutrient medium suitable for production of lysine, and the lysine content in the culture supernatant is determined.

For this purpose, the strain is first incubated on an agar plate at 33° C. for 24 hours. Starting from this agar plate culture, a preculture is inoculated (10 ml of medium in a 100 ml conical flask). The medium MM is used for said preculture. The preculture is incubated on a shaker at 240 rpm and 33° C. for 24 hours. A main culture is inoculated from this preculture so as to obtain an initial OD (660 nm) of the main culture of 0.5 OD. The medium MM is also used for the main culture.

| Medium MM | |
|---|---|
| CSL | 5 g/l |
| MOPS | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7H_2O$ | 1.0 g/l |
| $CaCl_2 * 2H_2O$ | 10 mg/l |
| $FeSO_4 * 7H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Homoserine (sterile-filtered) | 0.4 g/l |
| $CaCO_3$ | 25 g/l |

CSL (Corn Steep Liquor), MOPS (Morpholinopropanesulphonic acid) and the salt solution are adjusted to pH 7 with aqueous ammonia and autoclaved. The sterile substrate and vitamin solutions and also the $CaCO_3$, autoclaved in the dry state, are added thereafter.

Culturing is carried out in a volume of 10 ml in a 100 ml conical flask with baffles. Culturing is carried out at 33° C. and 80% humidity.

After 72 hours, the OD at a measurement wavelength of 600 nm is determined using an Ultrospec 3000 (Amersham Pharmacia Biotech GmbH, Freiburg). The amount of lysine produced is determined using an amino acid analyser from Eppendorf-BioTronik (Hamburg, Germany) by ion exchange chromatography and post-column derivatization with ninhydrin detection. Table 1 depicts the result of the experiment.

TABLE 1

| Strain | OD (600 nm) | Lysine g/l |
|---|---|---|
| DM1729 | 18.1 | 4.9 |
| DM1729deltasugR | 9.9 | 5.8 |

Example 6

Deletion Mutagenesis of the sugR Gene in ATCC13032delta aceE_deltapqo

The valine-producing *Corynebacterium glutamicum* strain ATCC13032delta aceE_deltapqo is a mutant of *Corynebacterium glutamicum* ATCC13032 (Schreiner, et al., *J. Bacteriol.* 188(4):1341-1350 (2006)).

The sugR gene was deleted as described in Example 4. The strain obtained was referred to as *C. glutamicum* ATCC13032deltaaceE_deltapqo_deltasugR.

*C. glutamicum* ATCC13032deltaaceE_deltapqo and *C. glutamicum* ATCC13032 deltaaceE_deltapqo_deltasugR were transformed with the plasmid pJC4ilvBNCE (Radmacher et al., Applied and Environmental Microbiology 68: 2246-2250 (2002)) according to Van der Rest, et al. (*Appl. Microbiol. Biotechnol.* 52:541-545 (1999)).

Example 7

Preparation of Valine

The *C. glutamicum* strain obtained in Example 6, ATCC13032deltaaceE_deltapqo deltasugR/pJC4ilvBNCE, is cultured in a nutrient medium suitable for production of valine, and the valine content in the culture supernatant is determined.

Comparative fermentations were carried out using the strains *C. glutamicum* ATCC13032deltaaceE_deltapqo/pJC4ilvBNCE and *C. glutamicum*ATCC13032delta aceE_deltapqo_deltasugR/pJC4ilvBNCE according to Blombach, et al. (*Appl. Environ. Microbiol.* 73(7):2079-2084 (2007)).

*C. glutamicum* ATCC13032deltaaceE_deltapqo/pJC4ilvBNCE and *C. glutamicum* ATCC13032deltaaceE_deltapqo_deltasugR/pJC4ilvBNCE were drawn by removing, using a sterile loop, cell suspension from a glycerol culture and streaking out said cell suspension on a tryptone yeast agar plate (tryptone 16 g/l; yeast extract 10 g/l; NaCl 5 g/l; agar 15 g/l) containing kanamycin (50 µg/ml) and additionally 0.5% (w/v) potassium acetate (KAc).

After incubating the agar plates at 30° C. for 48 hours, a colony was used for inoculating 5 ml of tryptone yeast medium (tryptone 16 g/l; yeast extract 10 g/l; NaCl 5 g/l) supplemented with 0.5% (w/v) KAc and kanamycin (50 µg/ml). After 6 h of incubation, the whole 5 ml were transferred to 50 ml of medium of the same composition and incubated overnight. For valine fermentation, the cells were pelleted by centrifugation (using a Centrifuge 5804 R, Eppendorf-Netheler-Hinz GmbH, Cologne, Germany at 5000 rpm; 4° C.; 10 min), washed with 20 ml of 0.9% (w/v) NaCl and added as inoculum to CgXII medium (Keilhauer, et al., *J. Bacteriol.* 175:5595-5603 (1993)) supplemented with 4% (w/v) glucose, 1% (w/v) KAc, 0.5% (w/v) brain-heart broth and kanamycin (50 µg/ml). *C. glutamicum* was cultured under aerobic conditions (500 ml conical flask with 2 baffles) on a rotary shaker at 120 rpm and 30° C.

The optical density (OD), and the substrate and product concentrations were determined after 11 hours (according to Blombach et al., *Appl. Environ. Microbiol.* 73(7):2079-2084 (2007)). Culture growth was determined photometrically (Ultrospec 3000, Amersham Pharmacia Biotech GmbH, Freiburg, Germany) on the basis of the optical density at a wavelength of 600 nm. An aliquot of 1 ml of cell suspension was centrifuged (in a bench centrifuge, type 5415D, (Eppendorf, Hamburg) at 13 000 rpm, 10 min, room temperature), and the supernatant was used for determining the substrate and product concentrations. The valine concentration was determined by means of reversed-phase high pressure liquid chromatography (HP 1100, Hewlett-Packard, Waldbronn, Germany) using a fluorescence detector after automated pre-column derivatization with ortho-phthaldialdehyde (OPA) (Lindroth, et al, *Anal. Chem.* 51:1667-1674 (1979)). Glucose and acetate concentrations were determined by enzymatic assays (Roche Diagnostics, Penzberg, Germany).

TABLE 2

Optical density (OD), substrate and product concentrations of the fermentation of *C. glutamicum* ATCC13032deltaaceE_deltapqo/pJC4ilvBNCE.
*C. glutamicum* ATCC13032deltaaceE_deltapqo/pJC4ilvBNCE

| Time [h] | OD [600 nm] | Glucose [g/l] | Acetate [g/l] | L-Valine [mM] |
|---|---|---|---|---|
| 0 | 1.02 | 35.2 | 12.5 | 0 |
| 11 | 54.0 | 27.3 | 0 | 1 |

TABLE 3

Optical density (OD), substrate and product concentrations of the fermentation of *C. glutamicum* ATCC13032deltaaceE_deltapqo_deltasugR/pJC4ilvBNCE.
*C. glutamicum* ATCC13032deltaaceE_deltapqo_deltasugR/pJC4ilvBNCE

| Time [h] | OD [600 nm] | Glucose [g/l] | Acetate [g/l] | L-Valine [mM] |
|---|---|---|---|---|
| 0 | 1.38 | 44.7 | 11.3 | 0 |
| 11 | 19.2 | 35 | 1.5 | 10.7 |

ABBREVIATIONS

The base pair numbers stated are approximate values obtained in the context of reproducibility of measurements. The abbreviations and designations used have the following meaning:

| | |
|---|---|
| oriV: | ColE1-like origin from pMB1 |
| sacB | The sacB gene coding for the protein levan sucrase |
| RP4-mob: | RP4-mobilization site |
| Kan: | Kanamycin resistance gene |
| LacZ-alpha': | 5' terminus of the lacZα gene fragment |
| 'LacZ-alpha: | 3' terminus of the lacZα gene fragment |
| sugR: | Deleted allele of the *C. glutamicum* sugR gene |
| BamHI: | Cleavage site of the restriction enzyme BamHI |
| EcoRI: | Cleavage site of the restriction enzyme EcoRI |
| PvuII: | Cleavage site of the restriction enzyme PvuII |

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for the fermentative production of an organic chemical compound, comprising:
   a) producing a fermentation broth by fermenting a recombinant coryneform bacterium in a medium comprising a carbon source selected from the group consisting of: glucose, fructose, sucrose, and acetic acid, wherein said recombinant coryneform bacterium:
      i) secretes said organic chemical compound;
      ii) has the ability to utilize as a carbon source one or more of the sugars selected from the group consisting of: glucose, fructose; sucrose, and acetic acid;
      iii) comprises a feedback resistant aspartate kinase; and
      iv) comprises a SugR regulator that comprises the sequence of SEQ ID NO:2 except for one or more differences selected from the group consisting of:
         aa) the amino acid at position 37 is selected from the group consisting of: L-alanine, glycine, L-isoleucine and L-proline;
         bb) the amino acid at position 38 is selected from the group consisting of: L-alanine, glycine, L-isoleucine and L-proline;
         cc) the amino acid at position 39 is selected from the group consisting of: L-alanine, glycine, L-isoleucine and L-proline;
         dd) the amino acid at position 40 is L-proline;
         ee) the amino acid at position 72 is selected from the group consisting of: L-alanine, glycine, L-glutamic acid and L-aspartic acid;
         ff) the amino acid at position 101 is selected from the group consisting of: L-arginine, L-lysine, L-phenylalanine, L-methionine, L-glutamine, L-tryptophan, L-tyrosine and L-glutamic acid;
         gg) the amino acid at position 105 is selected from the group consisting of: L-proline, L-phenylalanine, L-isoleucine, L-methionine, L-glutamine, L-tryptophan and L-tyrosine;
         hh) the amino acid at position 210 is selected from the group consisting of: L-alanine, L-arginine, and L-proline; and
         ii) the amino acid at position 216 is selected from the group consisting of: L-alanine, L-glutamic acid, L-isoleucine and L-tryptophan;
      and
   b) collecting said fermentation broth containing said organic chemical compound.

2. The process of claim 1, wherein the fermentation broth collected in step b) is dried.

3. The process of claim 1, wherein the fermentation broth collected in step b) is dried without the removal of biomass.

4. The process of claim 1, wherein biomass is removed from the fermentation broth of step b) so that not more than 30% of the biomass remains in the product thereby produced.

5. The process of claim 1, wherein said organic chemical compound is isolated from the fermentation broth of step b) so that not more than 0.1% of biomass remains in the product thereby produced.

6. The process of claim 1, wherein said organic chemical compound is a hydroxy acid or a keto acid.

7. The process of claim 1, wherein said organic chemical compound is an L-amino acid.

8. The process of claim 1, wherein said organic chemical compound is L-lysine, L-valine or L-isoleucine.

9. The process of claim 1, wherein said recombinant coryneform bacterium is of the species *Corynebacterium glutamicum*.

10. The process of claim 1, wherein said recombinant coryneform bacterium additionally possesses one or more of the features selected from the group consisting of:
 a) expression of a polynucleotide which codes for an aspartate-semialdehyde dehydrogenase (Asd) is increased compared to expression in a corresponding non-recombinant bacterium,
 b) expression of a polynucleotide which codes for a dihydrodipicolinate synthase (DapA) is increased compared to expression in a corresponding non-recombinant bacterium,
 c) expression of a polynucleotide which codes for a dihydrodipicolinate reductase (DapB) is increased compared to expression in a corresponding non-recombinant bacterium,
 d) expression of a polynucleotide which codes for a tetrahydrodipicolinate succinylase (DapD) is increased compared to expression in a corresponding non-recombinant bacterium,
 e) expression of a polynucleotide which codes for a succinyl-aminoketopimelate transaminase (DapC) is increased compared to expression in a corresponding non-recombinant bacterium,
 f) expression of a polynucleotide which codes for a succinyl-diaminopimelate desuccinylase (DapE) is increased compared to expression in a corresponding non-recombinant bacterium,
 g) expression of a polynucleotide which codes for a diaminopimelate dehydrogenase (Ddh) is increased compared to expression in a corresponding non-recombinant bacterium,
 h) expression of a polynucleotide which codes for a diaminopimelate epimerase (DapF) is increased compared to expression in a corresponding non-recombinant bacterium,
 i) expression of a polynucleotide which codes for a diaminopimelate decarboxylase (LysA) is increased compared to expression in a corresponding non-recombinant bacterium,
 j) expression of a polynucleotide which codes for a polypeptide having L-lysine export activity (LysE) is increased compared to expression in a corresponding non-recombinant bacterium,
 k) expression of a polynucleotide which codes for an aspartate aminotransferase (Aat) is increased compared to expression in a corresponding non-recombinant bacterium,
 l) expression of a polynucleotide which codes for a pyruvate carboxylase (Pyc) is increased compared to expression in a corresponding non-recombinant bacterium,
 m) elimination of malate-quinone oxidoreductase (Mqo) activity,
 n) elimination of malate dehydrogenase (Mdh) activity, and
 o) elimination of citrate synthase (GltA) activity;
 wherein the expression of polynucleotides encoding the enzymes in paragraphs a)-l) is increased by placing said polynucleotides under the control of a heterologous promoter or by increasing their copy number, and wherein the elimination of the activity of the enzymes of paragraphs m)-o) is due to the disruption of endogenous genes encoding the enzymes by making a deletion or insertion mutation in said endogenous genes.

11. A process for the fermentative production of an organic chemical compound, comprising:
 a) producing a fermentation broth by fermenting a recombinant coryneform bacterium in a medium comprising a carbon source selected from the group consisting of: glucose, fructose, sucrose, and acetic acid, wherein said recombinant coryneform bacterium:
  i) secretes said organic chemical compound;
  ii) has the ability to utilize as a carbon source one or more of the sugars selected from the group consisting of: glucose, fructose; sucrose, and acetic acid;
  iii) comprises a feedback resistant aspartate kinase; and
  iv) comprises a gene encoding the SugR regulator of SEQ ID NO:2, said gene comprising in its promoter region, the nucleotide sequence of SEQ ID NO:13 except for one or more mutations selected from the group consisting of:
   aa) replacement of the nucleobase thymine at position 7 of SEQ ID NO:13 by guanine;
   bb) deletion of one or more of the nucleobases from position 2 to 7 of SEQ ID NO:13;
   cc) deletion of one or more of the nucleobases between position 52 and 57 of SEQ ID NO:13; and
   dd) replacement of one or more of the nucleobases adenine or guanine between position 52 and 57 of SEQ ID NO:13 by thymine or cytosine;
  and
 b) collecting said fermentation broth containing said organic chemical compound.

12. The process of claim 11, wherein the fermentation broth collected in step b) is dried.

13. The process of claim 11, wherein the fermentation broth collected in step b) is dried without the removal of biomass.

14. The process of claim 11, wherein biomass is removed from the fermentation broth of step b) so that not more than 30% of the biomass remains in the product thereby produced.

15. The process of claim 11, wherein said organic chemical compound is isolated from the fermentation broth of step b) so that not more than 0.1% of biomass remains in the product thereby produced.

16. The process of claim 11, wherein said gene encoding the SugR regulator of SEQ ID NO:2 comprises a start codon selected from the group consisting of GTG and TTG.

17. The process of claim 11, wherein said organic chemical compound is a hydroxy acid or a keto acid.

18. The process of claim 11, wherein said organic chemical compound is an L-amino acid.

19. The process of claim 11, wherein said organic chemical compound is L-lysine, L-valine or L-isoleucine.

20. The process of claim 11, wherein said recombinant coryneform bacterium is of the species *Corynebacterium glutamicum*.

\* \* \* \* \*